(12) United States Patent
Bhide et al.

(10) Patent No.: US 6,969,717 B2
(45) Date of Patent: *Nov. 29, 2005

(54) AZAINDOLE KINASE INHIBITORS

(75) Inventors: Rajeev S. Bhide, Princeton Junction, NJ (US); Rejean Ruel, St-Lambert (CA); Carl Thibault, Mascouche (CA); Alexandre L'Heureux, Longueuil (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/622,593

(22) Filed: Jul. 18, 2003

(65) Prior Publication Data

US 2004/0063707 A1 Apr. 1, 2004

Related U.S. Application Data

(60) Provisional application No. 60/397,256, filed on Jul. 19, 2002, and provisional application No. 60/447,213, filed on Feb. 13, 2003.

(51) Int. Cl.$^7$ .................. C07D 484/04; A61K 31/53; A61P 13/08; A61P 29/00; A61P 37/00
(52) U.S. Cl. .................................. 514/243; 544/183
(58) Field of Search .......................... 544/183; 514/243

(56) References Cited

U.S. PATENT DOCUMENTS

2003/0069244 A1   4/2003   Leftheris et al.

FOREIGN PATENT DOCUMENTS

WO   WO0071129   11/2000

OTHER PUBLICATIONS

Cecil Textbook of Medicine, edited by Bennet, J.C., and Plum F., 20th edition,vol. 1, 1004–1010, 1996.*
Wolft Manfred E. "Burger's Medicinal Chemistry, 5ed, Part 1", John Wiley & Sons, 1995, pp. 975–977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Fan et al., Trend Pharmacol. Sci., vol. 16, pp. 57–66 (1995).
Folkman, Nature Medicine, vol. 1, pp. 27–31 (1995).
Cullinan–Bove et al., Endocrinology, vol. 133, pp. 829–837 (1993).
Senger et al., Cancer and Metastasis Reviews, vol. 12, pp. 303–324 (1993).
DeVries et al., Science, vol. 255, pp. 989–991 (1992).
Terman et al., Biochem. Biophys. Res. Comm., vol. 187, pp. 1579–1586 (1992).
Jakeman et al., Endocrinology, vol. 133, pp. 848–859 (1993).
Kolch et al., Breast Cancer Research and Treatment, vol. 36, pp. 139–155 (1995).
Connolly et al., J. Biol. Chem., vol. 264, pp. 20017–20024 (1989).
U.S. Appl. No. 10/289,010, filed Nov. 6, 2002, Pending.
U.S. Appl. No. 09/573,829, filed May 18, 2000, Pending.
U.S. Appl. No. 10/294,281, filed Nov. 14, 2002, Pending.
U.S. Appl. No. 10/633,997, filed Aug. 4, 2003, Pending.
U.S. Appl. No. 10/623,171, filed Jul. 18, 2003, Pending.
U.S. Appl. No. 10/420,399, filed Apr. 22, 2003, Pending.
U.S. Appl. No. 10/420,445, filed Apr. 22, 2003, Pending.
U.S. Appl. No. 10/440,864, filed May 19, 2003, Pending.

* cited by examiner

*Primary Examiner*—Venkataraman Balasubramanian
(74) *Attorney, Agent, or Firm*—Elliott Korsen

(57) ABSTRACT

The present invention provides compounds of formula I,

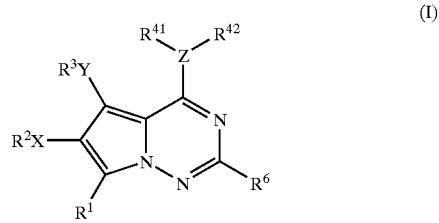

and pharmaceutically acceptable salts thereof.

The formula I compounds inhibit the tyrosine kinase activity of growth factor receptors such as VEGFR-2 and FGFR-1, thereby making them useful as anti-cancer agents. The formula I compounds are also useful for the treatment of other diseases associated with signal transduction pathways operating through growth factor receptors.

2 Claims, No Drawings

AZAINDOLE KINASE INHIBITORS

This application claims the priority benefit of U.S. Provisional Application No. 60/397,256 filed Jul. 19, 2002 and U.S. Provisional Application No. 60/447,213 filed Feb. 13, 2003, the disclosures of which are incorporated herein by reference in their entirety.

FIELD OF THE INVENTION

This invention relates to compounds that inhibit the tyrosine kinase activity of growth factor receptors such as VEGFR-2 and FGFR-1, thereby making them useful as anti-cancer agents. The compounds are also useful in the treatment of diseases, other than cancer, which are associated with signal transduction pathways operating through growth factors and anti-angiogenesis receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in EC activation. Disruption of these pathways should inhibit endothelial cell activation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

DETAILED DESCRIPTION OF THE INVENTION

In accordance with the present invention, compounds of formula I,

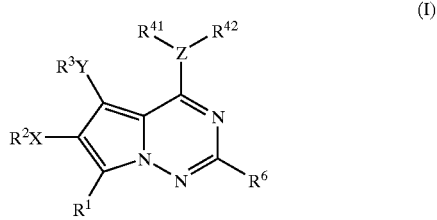

their enantiomers, diastereomers, and pharmaceutically acceptable salts, prodrugs and solvates thereof, inhibit the tyrosine kinase activity of growth factor receptors such as VEGFR-2. In formula I and throughout the specification, the above symbols are defined as follows:

Z is selected from O, S, N, OH, or Cl, with the provisos that when Z is O or S, $R^{41}$ is absent and when Z is OH or Cl, both $R^{41}$ and $R^{42}$ are absent;

X and Y are independently selected from O, OCO, S, SO, SO$_2$, CO, CO$_2$, NR$^{10}$, NR$^{11}$CO, NR$^{12}$CONR$^{13}$, NR$^{14}$CO$_2$, NR$^{15}$SO$_2$, NR$^{16}$SO$_2$NR$^{17}$, SO$_2$NR$^{18}$, CONR$^{19}$, halogen, nitro, cyano, or X or Y are absent;

R$^1$ is hydrogen, CH$_3$, OH, OCH$_3$, SH, SCH$_3$, OCOR$^{21}$, SOR$^{22}$, SO$_2$R$^{23}$, SO$_2$NR$^{24}$R$^{25}$, CO$_2$R$^{26}$, CONR$^{27}$R$^{28}$, NH$_2$, NR$^{29}$SO$_2$NR$^{30}$R$^{31}$, NR$^{32}$SO$_2$R$^{33}$, NR$^{34}$COR$^{35}$, NR$^{36}$CO$_2$R$^{37}$, NR$^{38}$CONR$^{39}$R$^{40}$, halogen, nitro, or cyano;

R$^2$ and R$^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heteroaryl, substituted heteroaryl, heterocycloalkyl or substituted heterocycloalkyl; with the proviso that when X is halo, nitro or cyano, R$^2$ is absent, and, when Y is halo, nitro or cyano, R$^3$ is absent;

R$^6$ is H, alkyl, substituted alkyl, aryl, substituted aryl, heterocyclo, substituted heterocyclo, NR$^7$R$^8$, OR$^9$ or halogen;

R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{21}$, R$^{24}$, R$^{25}$, R$^{26}$, R$^{27}$, R$^{28}$, R$^{29}$, R$^{30}$, R$^{31}$, R$^{32}$, R$^{34}$, R$^{35}$, R$^{36}$, R$^{38}$, R$^{39}$ and R$^{40}$ are independently selected from the group consisting of hydrogen, alkyl, substituted alkyl, aryl, substituted aryl, heteroaryl, substituted heteroaryl, heterocyclo, or substituted heterocyclo;

R$^{22}$, R$^{23}$, R$^{33}$ and R$^{37}$ are independently selected from the group consisting of alkyl, substituted alkyl, aryl, substituted aryl, heteroaryl, substituted heteroaryl, heterocyclo, or substituted heterocyclo;

R$^{42}$ is

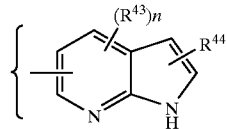

(R$^{43}$)$_n$ wherein n equals 0, 1 or 2 and each R$^{43}$ is independently selected from the group consisting of hydrogen, fluorine, chlorine and methyl; and R$^{44}$ is methyl, or hydrogen, with the further provisos that:

a. R$^2$ may not be hydrogen if X is SO, SO$_2$, NR$^{13}$CO$_2$, or NR$^{14}$SO$_2$; and b. R$^3$ may not be hydrogen if Y is SO, SO$_2$, NR$^{13}$CO$_2$, or NR$^{14}$SO$_2$.

In a preferred embodiment R$^1$ is hydrogen or methyl; R$^6$ is hydrogen; R$^3$ is lower alkyl; and Z is oxygen or nitrogen.

In another preferred embodiment R$^1$ is hydrogen; R$^3$ is lower alkyl; Y is absent; X is oxygen or nitrogen; R$^{43}$ is fluoro or hydrogen; and R$^{44}$ is hydrogen or methyl.

In yet another preferred embodiment X is oxygen; R$^2$ is a substituted alkyl and R$^{43}$ is fluoro.

In yet another preferred embodiment X is absent; R$^2$ is a substituted hetrocyclo, substituted heterocyclo, heteroaryl, substituted heteroaryl, and Z is nitrogen.

Preferred compounds of the invention include
4-(4-Fluoro-1H-pyrrolo[2,3-b]pyridin-5-yloxy)-5-methyl-pyrrolo[2,1-f][1,2,4]triazin-6-ol,
(R)-1-[4-(4-Fluoro-1H-pyrrolo[2,3-b]pyridin-5-yloxy)-5-methylpyrrolo[2,1-f][1,2,4]triazin-6-yloxy]-propan-2-ol,
(S)-1-[4-(4-Fluoro-1H-pyrrolo[2,3-b]pyridin-5-yloxy)-5-methyl-pyrrolo[2,1-f][1,2,4]triazin-6-yloxy]-propan-2-ol,
(R)-1-[4-(4-Fluoro-2-methyl-1H-pyrrolo[2,3-b]pyridin-5-yloxy)-5-methyl-pyrrolo[2,1-f][1,2,4]triazin-6-yloxy]-propan-2-ol,
(R)-2-[4-(4-Fluoro-1H-pyrrolo[2,3-b]pyridin-5-yloxy)-5-methylpyrrolo[2,1-f][1,2,4]triazin-6-yloxy]-1-methylethylamine,
(R)-2-[4-(4-Fluoro-2-methyl-1H-pyrrolo[2,3-b]pyridin-5-yloxy)-5-methylpyrrolo[2,1-f][1,2,4]triazin-6-yloxy]-1-methyl-ethylamine,
2-[4-(4-Fluoro-1H-pyrrolo[2,3-b]pyridin-5-yloxy)-5-methylpyrrolo[2,1-f][1,2,4]triazin-6-yloxy]-ethylamine,
(4-Fluoro-1H-pyrrolo[2,3-b]pyridin-5-yl)-[5-isopropyl-6-(3-methyl-[1,2,4]oxadiazol-5-yl)-pyrrolo[2,1-f][1,2,4]triazin-4-yl]-amine,
(4-Fluoro-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine,
(4-Fluoro-2-methyl-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine, and
[5-Isopropyl-6-(5-methyl-[1,3,4]oxadiazol-2-yl)-pyrrolo[2,1-f][1,2,4]triazin-4-yl]-(2-methyl-1H-pyrrolo[2,3-b]pyridin-5-yl)-amine.

The invention also provides a pharmaceutical composition comprising a compound of formula I or II and a pharmaceutically acceptable carrier.

The invention also provides a pharmaceutical composition comprising a compound of formula I or II in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; goserelin acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cisplatin; carboplatin; nitrogen mustard; melphalan; chlorambucil; busulphan; cyclophosphamide; ifosfamide nitrosoureas; thiotepa; vincristine; Taxol® (paclitaxel); Taxotere® (docetaxel); epothilone analogs; discodermolide analogs; eleutherobin analogs; etoposide; teniposide; amsacrine; topotecan; flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I.

Additionally, there is disclosed a method of inhibiting tyrosine kinase activity of at least one growth factor receptor such as which comprises administering to a mammalian species in need thereof, a therapeutically effective amount of a compound of formula I or II. In a preferred embodiment said growth factor receptor is selected from the group consisting of VEGFR-2 and FGFR-1.

Finally, there is disclosed a method for treating a proliferative disease, comprising administering to a mammalian species in need thereof, a therapeutically effective amount of a compound of formula I. In a preferred embodiment the proliferative disease is cancer.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, indole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered, bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzimidazolyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, excema, sclerodema, hemangioma. Compounds of the present invention posses good activity against VEGF receptor tyrosine kinase while possessing some activity against other tyrosine kinases.

Thus according to a further aspect of the invention, there is provided the use of a compound of formula I, or a pharmaceutically acceptable salt thereof in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of a compound of formula I or a pharmaceutically acceptable salt thereof as defined herein before.

The compounds described herein also inhibit other receptor tyrosine kinases including HER1 and HER2 and are therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. The ability of these compounds to inhibit HER1 further adds to their use as anti-angiogenic agents. See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000).

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines like 5-fluorouracil, purine and adenosine analogues, cytosine arabinoside); Intercalating antitumour antibiotics (for example, anthracyclines like doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids such as vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan); cell cycle inhibitors (for example, flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemnia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2 and FGFR-1.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may also be administered as suspensions using carriers appropriate to this mode of administration. The compounds may be administered in a dosage range of about 0.05 to 800 mg/kg/day, preferably less than 500 mg/kg/day, in a single dose or in 2 to 4 divided doses.

| VEGFR-2 and FGFR-1 Kinase assays: | | |
|---|---|---|
| Reagents | Final Concentration | |
| Stock Solution | VEGFR-2 | FGFR-1 |
| Tris pH 7.0 | 20 mM | 20 mM |
| BSA 10 mg/ml | 25 µg/ml | 25 µg/ml |
| MnCl$_2$ (1 M) | 1.5 mM | 0.5 mM |
| MgCl$_2$ (1 M) | — | 0.5 mM |
| DTT (1 M) | 0.5 mM | 0.5 mM |
| Enzyme Stock in 10% glycerol (1 mg/ml) | 7.5 ng/rxn | 30 ng/rxn |
| Poly glu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi/ml |

Incubation mixtures employed for VEGFR-2 or FGFR-1 assay contain the synthetic substrate poly glu/tyr, (4:1), ATP, ATP-γ-$^{33}$P and buffer containing Mn$^{++}$ and/or Mg$^{++}$, DTT, BSA, and Tris buffer. The reaction is initiated by addition of enzyme and after 60 minutes at room temperature is terminated by the addition of 30% TCA to a final concentration of 15% TCA. Inhibitors are brought to 10 mM in 100% DMSO. Assays are prepared in a 96 well format in quadruplicate. Compounds are diluted 1:500 in 100% DMSO and then 1:10 in water for a final DMSO concentration of 10%. 10 µL are added to rows B-H in a 96 well format of 10% DMSO. 20 µl of compound is added to row A at a concentration 5 fold higher than running conditions. Ten µL are transferred to each row followed by six serial dilutions with mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FilterMate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with IC$_{50}$ values between 0.001 to 10 µM. Preferred compounds have IC$_{50}$ values less than 0.3 µM against VEGFR-2.

These compounds are selective against VEGFR-2 and FGFR-1 kinase enzymes. They have minimum activity against HER-2, CDK kinases, LCK and Src kinases.

Methods of Preparation

Certain compounds of formula I may be prepared according to the following schemes and the knowledge of one skilled in the art.

All temperatures are in degrees Celsius (° C.) unless otherwise indicated. Preparative Reverse Phase (RP) HPLC purifications were done on: Premisphere® C-18-HC 21×100 mm column with solvent system (1) or (2). Solvent system (1): solvent A: 10% acetonitrile–90% water+5 mM NH$_4$OAc; solvent B: 90% acetonitrile–10% water+5 mM NH$_4$OAc. Solvent system (2): solvent A: 10% acetonitrile–90% water+0.05% TFA; solvent B: 90% acetonitrile–10% water+0.05% TFA. The gradient was with 20% B to 100% B. For LC/MS the conditions used were solvent system (1) or (2), with 0% B to 100% B in 2 minute gradient. Column: Premisphere C18-HC 4.6×30 mm, at 220 nM. Flow rate=4 mL/min). For analytical HPLC the conditions used were (solvent A: 10% acetonitrile–90% water+5 mM NH$_4$OAc; solvent B: 90% acetonitrile–10% water+5 mM NH$_4$OAc, with 0% B to 100% B in 30 minute gradient. Column YMC ODS-A C18, 6.0×150 mm, at 220 nM. Flow rate=4 mL/min.). All of the synthesized compounds were characterized by at least proton NMR and LC/MS (Micromass ZMD 2000, ESI). During work up of reactions, the organic extract was dried over anhydrous sodium sulfate (Na$_2$SO$_4$), unless mentioned otherwise.

The following abbreviations are used for the commonly used reagents. NMM; N-methylmorpholine, DIBAL; diisobutylaluminum hydride, BOP reagent; benzotriazol-1-yloxy-tris(trimethylamino)phosphonium hexafluorophosphate, DCE; dichloroethane, K$_2$CO$_3$; potassium carbonate, KOH; potassium hydroxide, DCC; dicyclohexyl carbodiimide, EDCI; 1-(dimethylaminopropyl)-3-ethylcarbodiimide hydrochloride, RT; room temperature, HOBt; hydroxybenzotriazole, DCM; dichloromethane, CbzCl; chlorobenzoyl chloride, mCPBA; meta-chloroperbenzoic acid, NaHCO$_3$; sodium bicarbonate, HCl; hydrochloric acid, TFA; trifluoroacetic acid, NH$_4$Cl; ammonium chloride, DIPEA; diisopropylamine, Et$_3$N; triethylamine. Na$_2$SO$_4$; sodium sulfate, DEAD; diethyl azodicarboxylate, DPPA; diphenylphosphorylazide, DMF; dimethyl formamide, THF; tetrahydrofuran, DBU; 1,8-diazabicyclo[5.4.0]undec-7-ene, RT; room temperature, min; minutes, h; hour Scheme 1

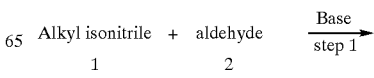

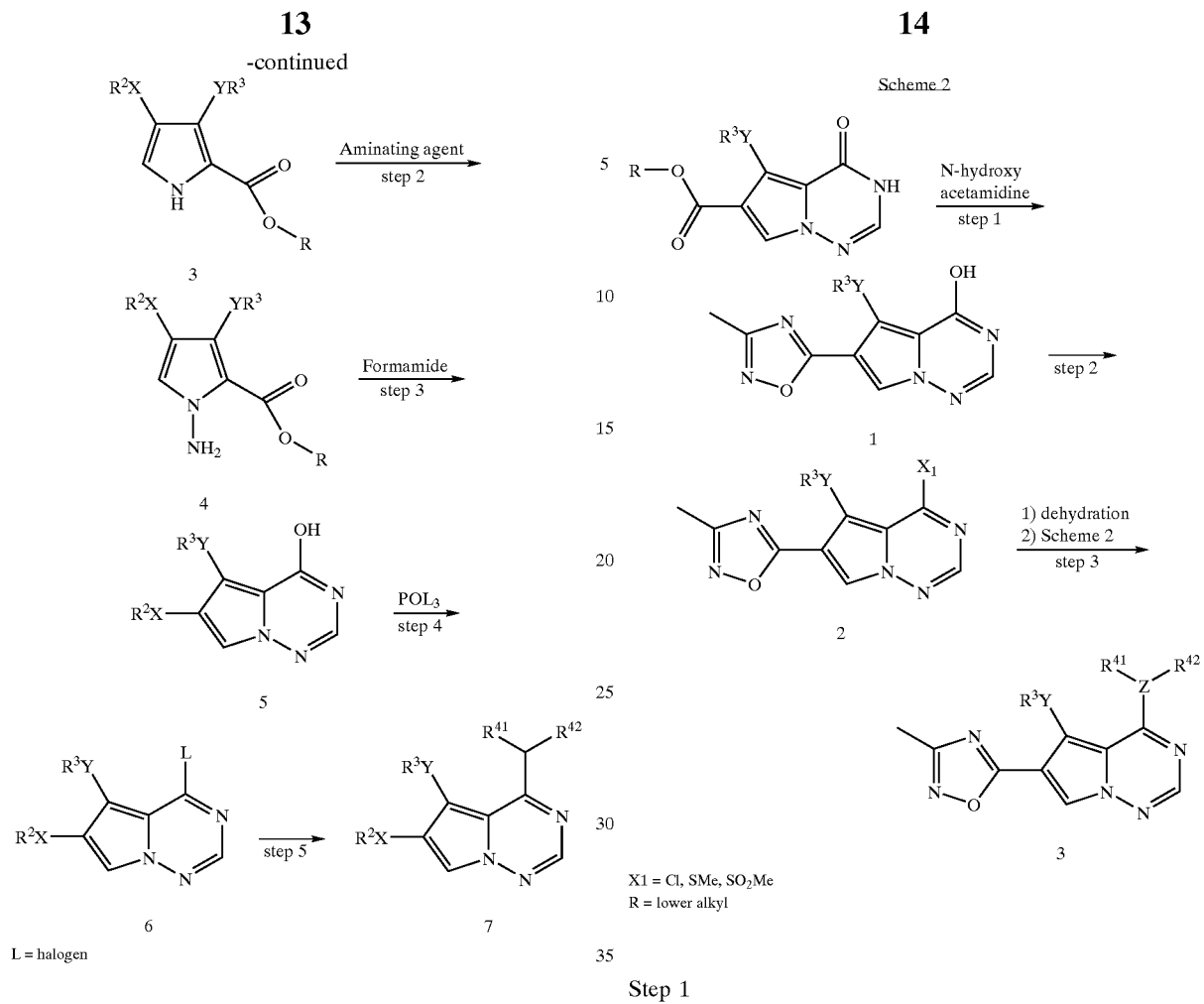

Step 1

This step is accomplished by the reaction of two equivalents of optionally substituted aldehyde (1) such as isobutyraldehyde, with alkyl isonitrile in the presence of a mild base like DBU to obtain compound 3.

Step 2

The product 3 of this scheme is reacted with an aminating reagent, such as hydroxylamine-O-sulfonic acid or O-2,4-dinitrophenylhydroxamate, in the presence of a base such as KOH or sodium hydride to form Compound 4.

Step 3

Compound 4 of this scheme is cyclized by treatment with formamide in the presence of a base such as sodium methoxide in MeOH with heating to afford Compound 5.

Step 4

Compound 5 of this scheme is halogenated, for example, with phosphorus oxychloride at elevated temperature, to afford Compound 6.

Step 5

Compound 6 is reacted with an amine such as an aniline, or a phenol, in an organic solvent, such as acetonitrile or DMF, to afford Compound 7.

Step 1

The pyrrolotriazine ester can be treated with an N-hydroxyacetamidine to obtain compound 1.

Step 2

Compound 2 of this scheme can then be treated with a halogenating agent such as phosphorous oxychloride, to obtain an intermediate chloroimidate.

Step 3

The chloroimidate obtained above, can be further treated with an appropriate aniline or phenol, can afford Compound 3 of this scheme as described in scheme 1.

-continued

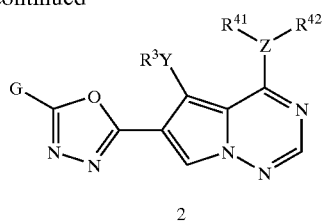

G = substituted methyl or methylene or substituted nitrogen or substituted sulfur etc.

Step 1
The pyrrolotriazine ester is treated with hydrazine hydrate to afford compound 1.

Step 2
Compound 1 can be then converted to compound 2 as described in Scheme 1.

Scheme 4

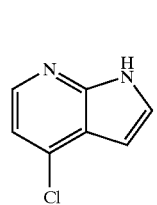 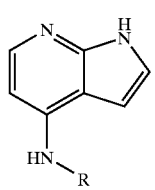 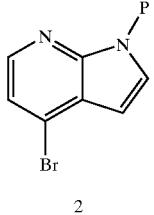

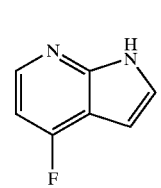 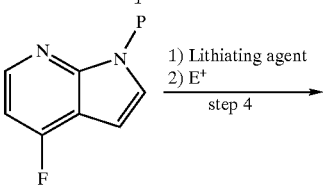 

X = O, N$_3$, NH$_2$
R = amine protecting group
P = Protecting group

Step 1
This step is accomplished by the reaction of 4-chloro-7-azaindole with an amine, such as allyl amine, in the presence of a catalyst, such as palladium (0), followed by deprotection of the aniline to obtain Compound 1 wherein R is a proton.

Step 2
Compound 1 of this scheme is reacted with sodium nitrite to form a diazonium salt which can be displaced by fluorine to form Compound 2.

Step 3
Compound 2 of this scheme is then protected, such as with a silyl protecting group, to form Compound 3 of Scheme 4.

Step 4
Compound 3 of this scheme is lithiated, for example, with sec-butyl lithium at low temperature, followed treatment with an electrophile, such as azide or oxirane, to form Compound 4 of Scheme 4. When using the azide, the compound may be further treated with palladium on carbon in the presence of hydrogen to obtain an aniline.

Step 5

Compound 4 is deprotected, to form Compound 5 of Scheme 4.

Scheme 5

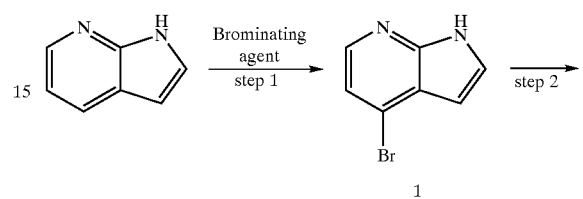

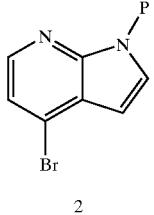

X = O, N$_3$, NH$_2$
P = Protecting group

Step 1

This step is accomplished by the reaction of 7-azaindole-N-oxide with a brominating agent, such as tetramethylammonium bromide, in the presence of methanesulfonic anhydride to obtain Compound 1.

Step 2

Compound 1 of this scheme is protected with a protecting group such as triisopropyl silane to obtain compound 2 of this scheme.

Step 3

Compound 2 of this scheme is then lithiated by halogen exchange followed by treatment with a fluorinating agent such as N-fluorobenzenesulfonimide to obtain Compound 3 of scheme 5.

Step 4

Compound 3 of this scheme can then be converted to Compound 4 as described in scheme 4.

Scheme 6

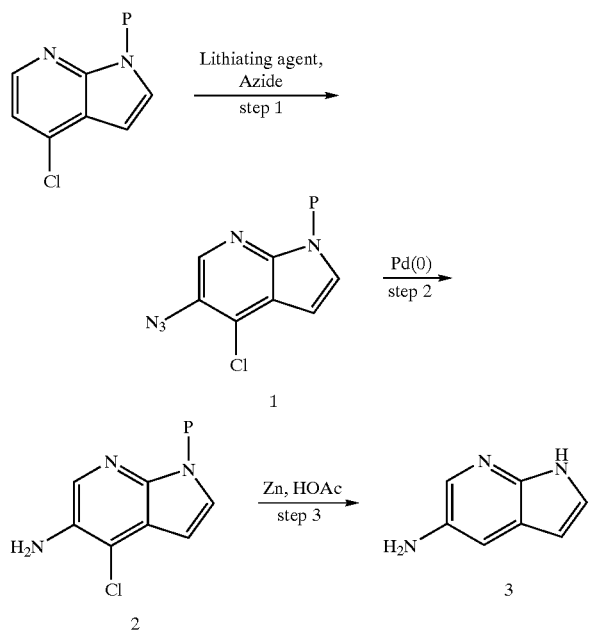

Step 1

This step is accomplished by the 5-lithiation of 4-chloro-7-azaindole with, for example, sec-butyl lithium at low temperature, followed by quenching with an azide, such as 4-azido toluene, to obtain Compound 1.

Step 2

Compound 1 of this scheme is reduced with hydrogen in the presence of a palladium catalyst, preferably palladium on carbon, to obtain Compound 2 of this scheme.

Step 3

Compound 2 of this scheme can then be further reduced with a dehalogenating agent, such as zinc dust, in the presence of acetic acid to obtain compound 3 of this scheme.

Scheme 7

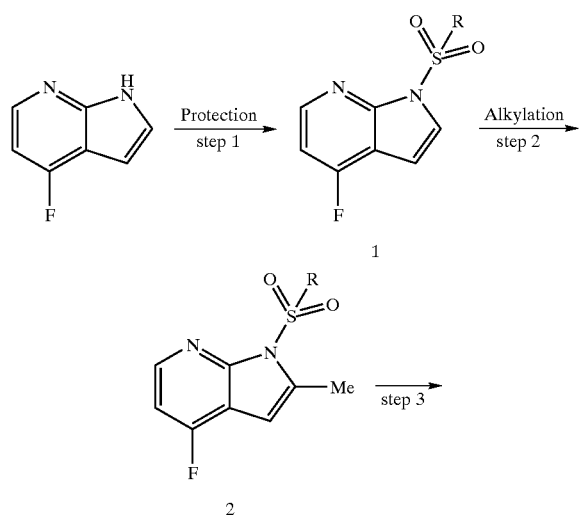

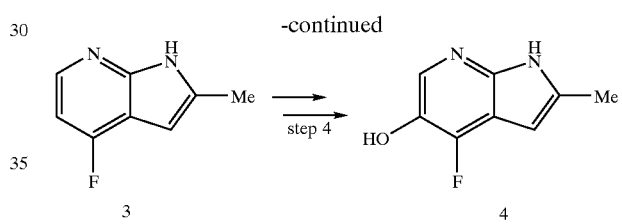

Step 1

The 4-fluoro-7-azaindole is protected by an appropriate protecting group such as phenyl sulfonamide to afford Compound 1 of Scheme 7.

Step 2

Compound 1 of this scheme is lithiated, for example, with n-butyl lithium at low temperature, followed by treatment with an electrophile, such as iodomethane to form Compound 2 of Scheme 7.

Step 3

Compound 2 of this scheme is then deprotected with a reagent such as tetrabutylammonium fluoride to afford Compound 3 of Scheme 7.

Step 4

Compound 3 of this scheme can then be converted to obtain Compound 4 as previously described.

In addition, other compounds of formula I may be prepared using procedures generally known to those skilled in the art. In particular, the following examples provide additional methods for preparing compounds of this invention.

The invention will now be further described by the following working examples, which are preferred embodiments of the invention. These examples are illustrative rather than limiting, and it is to be understood that there may be other embodiments that fall within the spirit and scope of the invention as defined by the claims appended hereto.

EXAMPLE 1

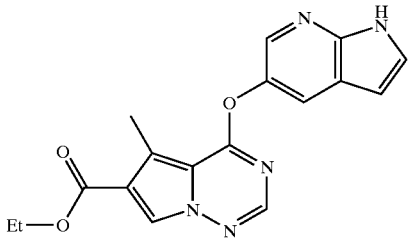

5-Methyl-4-(1H-pyrrolo[2,3-b]pyridin-5-yloxy)-pyrrolo[2,1-f][1,2,4]triazine-6- carboxylic acid ethyl ester At 0° C., sodium hydride (14 mg, 0.36 mmol, 60% in oil) was added to a solution of 5-hydroxy-7-azaindole (48 mg, 0.36 mmol) in DMF (1.5 mL) 4-chloro-5-methylpyrrolo[2,1-f][1,2,4]triazine-6-carboxylic acid ethyl ester (76 mg, 0.32 mmol, WO 0071129) was then added and the mixture was stirred at RT for 16 h, quenched with saturated ammonium chloride (20 mL) and extracted with ethyl acetate (3×25 mL). The combined organic layers were washed with brine (50 mL), dried, filtered and concentrated. The residue was purified by preparative HPLC (Retention time=7.12 min). $^1$H NMR (400 MHz, CDCl$_3$) δ 8.10(1H, s), 7.91 (1H, br. s), 7.82 (1H, s), 7.31 (1H, s), 6.85 (1H, br. s) 4.31 (2H, q, J=7.3 Hz), 2.79 (3H, s), 1.33 (3H, t, J=7.3 Hz). m/z 338 (M+H)$^+$, 379 (M+AcCN)$^+$.

The indole intermediate, 5-hydroxy-7-azaindole, was prepared as follows.

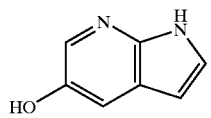

Under argon in a flask covered with aluminum foil, a solution of 5-methoxy-7-azaindole (60 mg, 0.4 mmol, for preparation see *Heterocycles* 1999, 50(2), 1065–1080) in dichloromethane was added to a solution of boron tribromide (890 μL, 1M) in dichloromethane at 78° C. The mixture was allowed to warm to RT and stirred for an additional 2 h. A 10% solution of sodium bicarbonate was then added and the separated aqueous layer was extracted with dichloromethane (3×25 mL). The combined organic layers were washed with brine (30 mL), dried, filtered and concentrated to yield 50 mg of an oil which was used directly without any further purification. m/z 135 (M+H)$^+$.

EXAMPLE 2

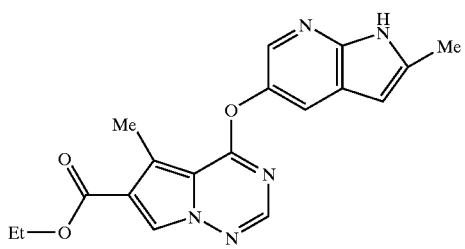

5-Methyl-4-(2-methyl-1H-pyrrolo[2,3-b]pyridin-5-yloxy)-pyrrolo[2,1-f][1,2,4]triazine-6-carboxylic acid ethyl ester The procedure described above for the preparation of Example 1 was applied using intermediate 5-hydroxy-2-methyl-7-azaindole. $^1$H NMR (400 MHz, CDCl$_3$) δ 8.87 (1H, br. s), 8.09 (1H, s), 8.06 (1H, br. s), 7.82 (1H, s), 7.60 (1H, br. s), 6.14 (1H, br. s), 4.31 (2H, q, J=7.0 Hz), 2.79 (3H, s), 2.43 (3H, s), 1.33 (3H, t, J=7.0 Hz). LC/MS; (M+H)$^+$= 352, (M+AcCN)=393.

The intermediate, 5-hydroxy-2-methyl-7-azaindole, was prepared as follows.

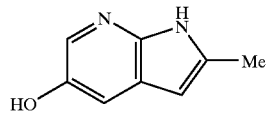

A. To a solution of 5-methoxy-7-azaindole (240 mg, 1.62 mmol) in THF (10 mL) was added a 60% suspension of sodium hydride in oil (71 mg, 1.78 mmol) at RT under argon. The mixture was stirred at RT for 5 minutes and phenylsulphonyl chloride (250 μL, 1.95 mmol) was added and the mixture was stirred for 16 h, quenched with saturated ammonium chloride (20 mL) and extracted with ethyl acetate (3×25 μL). The combined organic layers were washed with brine (50 mL), dried, filtered and concentrated. The residue was purified by flash chromatography (1% MeOH in dichloromethane+0.5% triethylamine) to afford N-phenylsulphonyl-5-methoxy-7-azaindole (325 mg, 70%) as a solid. $^1$H NMR (400 MHz, CDCl$_3$) δ 8.12 (3H, m), 7.65 (1H, dd, J=3.8), 7.54 (1H, m), 7.45 (2H, m), 7.28 (1H, d, J=2.8 Hz), 6.51 (1H, d, J=3.8 Hz), 3.82 (3H, s). (M+H)$^+$= 289.

B. A solution (2.7M) of n-butyllithium in hexanes (0.48 mL, 1.30 mmol) was added to a solution of N-phenylsulphonyl-5-methoxy-7-azaindole (220 mg, 0.76 mmol) in THF (7.0 mL) at −78° C. under argon. The resulting solution was stirred at −78° C. for 1 h and methyl iodide (120 μL, 1.91 mmol) was added. The resulting mixture was stirred at −78° C. for 2 h, quenched with saturated ammonium chloride (20 mL) and extracted with ethyl acetate (3×25 mL). The combined organic layers were washed with brine (50 mL), dried, filtered and concentrated. The residue was purified by flash chromatography (1% MeOH in dichloromethane+ 0.1% triethylamine) to afford (170 mg, 73%) of a (5:1) mixture of N-phenylsulphonyl-5-methoxy-2-methyl-7-azaindole, m/z 303 (M+H$^+$), analytical HPLC retention time=1.83 min and N-tolylsulphonyl-5-methoxy-2-methyl-7-azaindole, m/z 317, retention time=1.97 min.

C. To a solution of above mixture of compounds in (3:1) THF-methanol (4 mL) was added a 10% solution of sodium hydroxide in water (3 mL) at room temperature. The mixture was heated to 65° C. for 1 h, cooled to room temperature, neutralized to pH 7 with a saturated ammonium chloride solution and extracted with ethyl acetate (3×15 mL). The combined organic layers were washed with brine (50 mL), dried (Na$_2$SO$_4$), filtered and concentrated. The residue was purified by flash column chromatography on silica gel (1% MeOH in dichloromethane+0.1% triethylamine) to afford 5-methoxy-2-methyl-7-azaindole (35 mg, 66%). (M+H)$^+$= 163.

D. The procedure described above for the preparation of hydroxyindole from methoxyindole in Example 1 was applied to 5-methoxy-2-methyl-7-azaindole (35 mg, 0.2 mmol) to afford 5-hydroxy-2-methyl-7-azaindole (32 mg, 100%) which was used directly without any further purification. LC/MS; (M+H)$^+$=135.

EXAMPLE 3

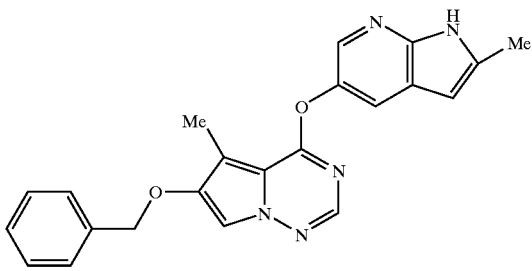

6-Benzyloxy-5-methyl-4-(2-methyl-1H-pyrrolo[2,3-b]pyridin-5-yloxy)-pyrrolo[2,1-f][1,2,4]triazine 5-Hydroxy-2-methyl-7-azaindole was treated with of 6-benzyloxy-4-chloro-5-methyl-pyrrolo[2,1-f][1,2,4]triazine (see WO 0071129) by a method similar to the preparation of Example 1. $^1$H NMR (400 MHz, DMSO-$d_6$) δ 8.02 (1H, br. s), 7.85 (1H, s), 7.83 (1H, s), 7.70 (1H, br. s), 7.41 (6H, m), 6.15 (1H, br. s), 5.12 (2H, s) 2.92 (3H, s), 2.42 (3H, s). m/z 386 (M+H)$^+$, 427 (M$^+$+AcCN).

EXAMPLE 4

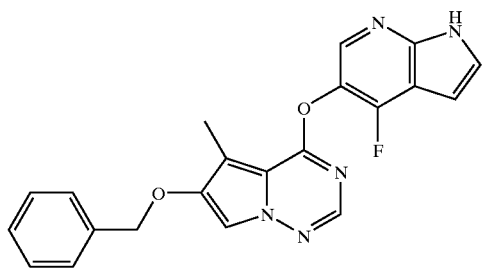

6-Benzyloxy-4-(4-fluoro-1H-pyrrolo[2,3-b]pyridin-5-yloxy)-5-methyl-pyrrolo[2,1-f][1,2,4]triazine To a solution of 4-fluoro-1H-pyrrolo[2,3-b]pyridin-5-ol (53.5 mg, 0.35 mmol) in DMF (2 mL) at −78° C., sodium hydride (60% in oil, 14 mg, 0.35 mmol) was added and the mixture was warmed to 0° C. After 30 minutes, the flask was cooled to −78° C., 6-benzyloxy-4-chloro-5-methyl-pyrrolo[2,1-f][1,2,4]triazine (80 mg, 0.29 mmol) was added and the mixture was allowed to reach RT over 30 min. A solution of saturated ammonium chloride was added, the solution was extracted with ethyl acetate (3×15 mL), combined organic layers were washed with water (30 mL), brine (30 mL), dried, and concentrated in vacuo. The crude material was purified by trituration with acetonitrile to give the title compound (90 mg, 80%) as an off-white solid. $^1$H NMR (400 MHz, DMSO-$d_6$) δ 12.17 (1H, s), 8.30 (1H, d, J=9.6 Hz), 8.00 (1H, s), 7.94 (1H, s), 7.61 (1H, t, J=3.0 Hz), 7.49 (2H, d, J=7.1 Hz), 7.41 (2H, t, J=7.1 Hz), 7.34 (1H, t, J=7.3 Hz), 6.59 (1H, dd, J=2.0, 3.5 Hz), 5.16 (2H, s), 2.43 (3H, s). LC/MS; (M+H)$^+$=m/z 390.

The intermediate, 4-fluoro-1H-pyrrolo[2,3-b]pyridin-5-ol, was prepared as follows.

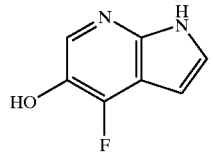

A. The procedure described in *J. Org. Chem.*, 2000, 65, 1158–1174 was followed. A 350-mL oven-dried flask capped with a rubber septum was evacuated and filled with argon. The flask was charged with 4-chloro-1H-pyrrolo[2,3-b]pyridine [20 g, 131 mmol, for preparation see Benoit, S.; Gingras, S. Processes for the preparation of antiviral 7-azaindole derivatives. U.S. Provisional Patent 60/367,401, 2003], sodium tert-butoxide (35.2 g, 367 mmol), Pd(OAc)$_2$ (589 mg, 2.62 mmol), (o-biphenyl)PCy$_2$ (1.83 g, 5.24 mmol) and evacuated and filled with argon. 1,4-dioxane (0.25 L) and N-allylamine (29 mL, 393 mmol) was added and argon was bubbled through the mixture for 20 minutes. The septum was replaced with a Teflon® screwcap, the flask was sealed and the mixture was heated at 100° C. for 16 h. The mixture was cooled to room temperature, diluted with ether (0.5 L), filtered through Celite® and concentrated in vacuo. The resulting oil was dissolved in dichloromethane (0.25 L), washed twice with water, dried, filtered and concentrated in vacuo to give allyl-(1H-pyrrolo[2,3-b]pyridin-4-yl)-amine as a brown gum. $^1$H NMR (400 MHz, DMSO-$d_6$) δ 11.10 (1H, br. s), 7.78 (1H, d, J=5.3Hz), 7.03 (1H, s), 6.73 (1H, t, J=5.8 Hz), 6.53 (1H, d, J=2.5 Hz), 6.04 (1H, t, J=5.5 Hz), 5.96–5.87 (1H, m), 5.22 (1H, ddd, J=1.8, 3.4, 17.2 Hz), 5.11 (1H, ddd, J=0.7, 1.8, 10.4 Hz), 3.86 (2H, m). LC/MS: m/z 174 (M+H)$^+$.

B. The procedure described in *Tetrahedron Letters*, 1998, 39, 1313–1316, was employed. A 0.5 L oven-dried round-bottom flask equipped with a condenser was evacuated and filled with argon. The flask was charged with allyl-(1H-pyrrolo[2,3-b]pyridin-4-yl)-amine (22.69 g, 131 mmol), ethanol (262 mL), 10% palladium on carbon (15 g) and methanesulfonic acid (8.5 mL, 131 mmol). The mixture was heated at 105° C. for 72 h. The mixture was cooled to room temperature, filtered through Celite and concentrated in vacuo. The resulting oil was purified by SCX-silica column (300 g), by eluting methanol (3×500 mL) followed by a solution of 2M ammonia in methanol (3×500 mL) to give 1H-pyrrolo[2,3-b]pyridin-4-ylamine (13.15 g, 75% over two steps) as a light yellow oil. $^1$H NMR (400 MHz, DMSO-$d_6$) δ 11.02 (1H, br. s), 7.69 (1H, d, J=5.3 Hz), 7.01 (1H, d, J=3.3 Hz), 6.46 (1H, d, J=3.3 Hz), 6.10 (1H, d, J=5.3 Hz), 6.07 (2H, s). LC/MS m/z 134 (M+H)$^+$.

C. 1H-Pyrrolo[2,3-b]pyridin-4-ylamine (10.3 g, 77 mmol) was dissolved in a 48% wt. solution of tetrafluoroboric acid in water (155 mL). The mixture was cooled to 0° C. and sodium nitrite (5.87 g, 85.1 mmol) in water (15 mL) was added dropwise. The mixture was allowed to reach RT and stirred for 22 h. Ethyl acetate was added (500 mL), the mixture was cooled to 0° C., neutralized with solid sodium hydrogen carbonate and the layers were separated. The aqueous layer was extracted with ethyl acetate (2×300 mL), the organic layers were combined and concentrated in vacuo. The resulting solid was triturated with 250 mL of ethyl acetate, filtered and the filtrate was washed with a solution of 1N sodium hydroxide (2×200 mL). The organic layer was dried, filtered and concentrated in vacuo to give 4-fluoro-1H-pyrrolo[2,3-b]pyridine (4.67 g, 44%) as a brown solid. ¹H NMR (400 MHz, DMSO-d₆) δ 12.00 (1H, br. s), 8.20 (1H, dd, J=5.3, 8.4 Hz), 7.51 (1H, t, J=3.1 Hz), 6.94 (1H, dd, J=5.3, 10.4 Hz), 6.51 (1H, dd, J=2.1, 3.6 Hz), 6.07 (2H, s). LCMS: m/z 134 (M+H)⁺.

D. 4-Fluoro-1H-pyrrolo[2,3-b]pyridine (2 g, 14.7 mmol) was dissolved in THF (50 mL) and sodium hydride (60% in oil, 881 mg, 22.0 mmol) was added in small portions. After 30 minutes, chlorotriisopropylsilane (4.71 mL, 22.0 mmol) was added and stirred at 65° C. for 16 h. Ethyl acetate was added (100 mL), the mixture was cooled at 0° C., neutralized with a solution of saturated ammonium chloride and the layers were separated. The aqueous layer was extracted twice with ethyl acetate (2×100 mL) and the organic layers were combined, washed with water (150 mL), brine (150 mL), dried, and concentrated in vacuo. The crude material was purified by flash chromatography eluting with 1% ethyl acetate in hexane to give 4-fluoro-1-triisopropylsilanyl-1H-pyrrolo[2,3-b]pyridine (2.16 g, 50%) as a colorless oil. ¹H NMR (400 MHz, DMSO-d₆) δ 8.22 (1H, dd, J=5.6, 8.3 Hz), 7.51 (1H, d, J=3.6 Hz), 6.98 (1H, dd, J=4.1, 10.1 Hz), 6.69 (1H, d, J=3.5 Hz), 1.86 (3H, m), 1.06 (9H, s), 1.04 (9H, s). LC/MS: m/z 293 (M+H)⁺.

E. The procedure described in *J. Med. Chem.*, 1997, 40, 2674 was modified. 4-Fluoro-1-triisopropylsilanyl-1H-pyrrolo[2,3-b]pyridine (213 mg, 0.73 mmol) was dissolved in THF (4.9 mL) and the mixture was cooled to −78° C. Sec-Butyllithium solution (1.10 M in THF, 1.46 mL, 1.61 mmol) was added dropwise and after 30 minutes, (R)-camphorsulfonyl oxaziridine (418 mg, 1.82 mmol) in tetrahydrofuran (2.5 mL) was added rapidly. After 25 min, a solution of saturated ammonium chloride was added and the mixture was allowed to reach RT. The solution was extracted with ethyl acetate (3×15 mL) and the combined organic layers were washed with water (30 mL), brine (30 mL), dried, and concentrated in vacuo. The crude material was purified by flash chromatography eluting a mixture of 5% ethyl acetate in toluene to give the desired product. LC/MS: m/z 309 (M+H)⁺.

F. 4-Fluoro-1-triisopropylsilanyl-1H-pyrrolo[2,3-b]pyridin-5-ol (207 mg, 0.67 mmol), THF (3.4 mL) and a solution of tetrabutylammonium fluoride (1.0 M in THF, 1.01 mL, 1.01 mmol) were added and the mixture was stirred for 90 min. A solution of saturated ammonium chloride was added and the mixture was extracted with ethyl acetate (3×15 mL), the combined organic layers were washed with water (30 mL), brine (30 mL), dried, and concentrated in vacuo. The crude material was purified by flash chromatography eluting a mixture of 1% NH₄OH: 7% methanol: 92% dichloromethane to afford 4-fluoro-1H-pyrrolo[2,3-b]pyridin-5-ol (60 mg, 59%) as a light yellow solid. ¹H NMR (400 MHz, DMSO-d₆) δ 11.62 (1H, s), 9.34 (1H, s), 7.95 (1H, d, J=10.3 Hz), 7.39 (1H, d, J=2.8 Hz), 6.38 (1H, dd, J=2.0, 3.2 Hz). LC/MS: m/z 153 (M+H)⁺.

EXAMPLE 5

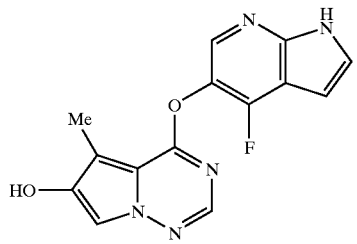

4-(4-Fluoro-1H-pyrrolo[2,3-b]pyridin-5-yloxy)-5-methyl-pyrrolo[2,1-f][1,2,4]triazin-6-ol To a solution of Example 4 (84 mg, 0.22 mmol) in DMF (1.1 mL), 10% Pd on charcoal (10 mg) and ammonium formate (68 mg, 1.08 mmol) were added. The mixture was stirred at RT for 20 h then filtered through Celite® and concentrated in vacuo. The resulting solid was dissolved in methanol and purified by SCX-silica column (18 g) by washing with methanol (2×8 mL) and then by eluting a solution of 2M ammonia in methanol (2×8 mL) to give the title compound (60 mg, 93%) as a beige solid. ¹H NMR (400 MHz, DMSO-d₆) δ 12.16 (1H, s), 9.53 (1H, s), 8.29 (1H, d, J=9.6 Hz), 7.88 (1H, s), 7.61 (1H, t, J=3.0 Hz), 7.55 (1H, s), 6.59 (1H, dd, J=2.0, 3.5 Hz), 2.40 (3H, s). LC/MS=m/z 300 (M+H)⁺.

EXAMPLE 6

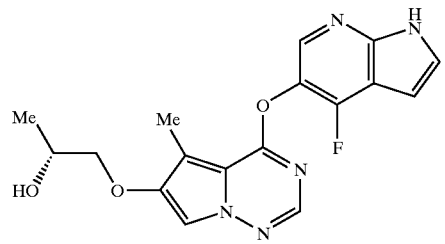

(R)-1-[4-(4-Fluoro-1H-pyrrolo[2,3-b]pyridin-5-yloxy)-5-methylpyrrolo[2,1-f][1,2,4]triazin-6-yloxy]-propan-2-ol An oven dried sealed tube was charged with 4-(4-fluoro-1H-pyrrolo[2,3-b]pyridin-5-yloxy)-5-methylpyrrolo[2,1-f][1,2,4]triazin-6-ol (Example 5) (7.5 mg, 0.025 mmol), t-BuOH (0.25 mL), 0.5M of a solution of triethylamine in t-BuOH (5 μL, 0.0025 mmol) and R-(+)-propylene oxide (21 μL, 0.300 mmol). The tube was sealed and the mixture was stirred at 80° C. for 1 h. The reaction mixture was cooled and concentrated in vacuo. The crude material was purified by preparative HPLC to afford the title compound (5 mg, 56%) as a off-white solid. ¹H NMR (400 MHz, DMSO-d₆) δ 12.17 (1H, s), 8.31 (1H, d, J=9.6 Hz), 7.95 (1H, s), 7.93 (1H, s), 7.61 (1H, t, J=3.0 Hz), 6.59 (1H, dd, J=1.9, 3.4 Hz), 4.91 (1H, d, J=4.8 Hz), 4.02–3.94 (1H, m), 3.92–3.83 (2H, m), 2.42 (3H, s), 1.16 (3H, d, J=6.3 Hz). LCMS: (M+H)⁺=358, (M−H)⁻=356.

EXAMPLE 7

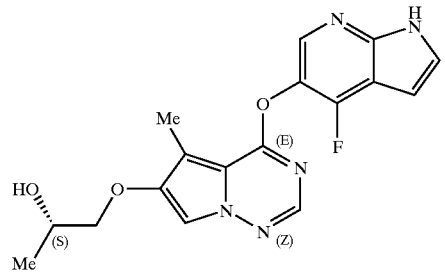

(S)-1-[4-(4-Fluoro-1H-pyrrolo[2,3-b]pyridin-5-yloxy)-5-methyl-pyrrolo[2,1-f][1,2,4]triazin-6-yloxy]-propan-2-ol A. A 150 mL tube was charged with 5-methyl-4-phenoxy-pyrrolo[2,1-f][1,2,4]triazin-6-ol (5.93 g, 24.6 mmol), THF (2 mL) and sodium methanethiol (5.17 mg, 73.7 mmol). The tube was sealed and the mixture was heated at 80° C. for 4 h. The mixture was cooled to RT, water was added (100 mL)

and the solution was extracted with ethyl acetate (3×100 mL). Combined organic layers were washed with water (200 mL), 1N aqueous solution of sodium hydroxide (2×200 mL), brine (200 mL), dried and concentrated in vacuo to afford (3.2 g, 67%) of 5-methyl-4-methylsulfanylpyrrolo[2,1-f][1,2,4]triazin-6-ol as an beige solid. $^1$H NMR (400 MHz, DMSO-$d_6$) δ 9.49 (1H, s), 8.11 (1H, s), 7.39 (1H, s), 2.58 (3H, s), 2.34 (1H, s). m/z 196 (M+H$^+$).

B. A 10 mL tube was charged with 5-methyl-4-methylsulfanylpyrrolo[2,1-f][1,2,4]triazin-6-ol (75 mg, 0.38 mmol), tert-butylalcohol (2 mL), (S)-propylene oxide (0.134 mL, 1.92 mmol) and triethylamine (5 μL, 0.04 mmol). The tube was sealed and the mixture was heated at 80° C. for 17 h. The mixture was cooled to RT and concentrated in vacuo. The crude material was purified by flash chromatography eluting a mixture of 50% ethyl acetate in hexane to give (56 mg, 58%) of (S)-1-(5-methyl-4-methylsulfanylpyrrolo[2,1-f][1,2,4]triazin-6-yloxy)-propan-2-ol as an white solid. $^1$H NMR (400 MHz, DMSO-$d_6$) δ 8.16 (1H, s), 7.78 (1H, s), 4.88 (1H, m), 3.95 (m, 1H), 3.82 (2H, m), 2.59 (3H, s), 2.36 (3H, s), 1.13 (3H, d, J=6.3 Hz). m/z 254 (M+H$^+$).

C. To a solution of (S)-5-methyl-4-methylsulfanyl-pyrrolo[2,1-f][1,2,4]triazin-6-ol (20 mg, 0.08 mmol) in chloroform (1.0 mL) at 0° C., was added a solution of peracetic acid in acetic acid (51 μL, 0.24 mmol, 32% wt solution). The mixture was allowed to reach RT and stirred for an additional 2.0 h. A saturated solution of ammonium chloride was added and the layers were separated. The aqueous layer was extracted with ethyl acetate (2×50 mL), the organic layers were combined, washed with water (100 mL), brine (100 mL), dried and concentrated in vacuo. The resulting sulfone was used without any purification.

D. At −78° C., sodium hydride (60% in oil, 3.1 mg, 0.08 mmol) was added to a solution of 4-fluoro-1H-pyrrolo[2,3-b]pyridin-5-ol (13 mg, 0.09 mmol, see Example 4) in dimethyl formamide (1 mL). The mixture was stirred at 0° C. for 30 min. and cooled back down to −78° C. (S)-1-(4-methanesulfonyl-5-methylpyrrolo[2,1-f][1,2,4]triazin-6-yloxy)-propan-2-ol (22 mg, 0.08 mmol) was then added and the mixture was stirred at RT for 2 h, quenched with saturated ammonium chloride (20 mL) and extracted with ethyl acetate (3×25 mL). The combined organic layers were washed with brine (50 mL), dried (MgSO$_4$), filtered and evaporated. The residue was purified by preparative HPLC to yield (10 mg, 36%) of the title compound. $^1$H NMR (400 MHz, DMSO-$d_6$) δ 12.17 (1H, s), 8.31 (1H, d, J=9.3 Hz), 7.95 (1H, s), 7.93 (1H, s), 7.61 (1H, t, J=3.1 Hz), 6.59 (1H, dd, J=1.98, 3.3 Hz), 4.01–3.97 (1H, m), 3.92–3.83 (2H, m), 2.42 (3H, s), 1.16 (3H, d, J=6.3 Hz). m/z 358 (M+H$^+$).

The azaindole intermediate 4-Fluoro-1H-pyrrolo[2,3-b]pyridin-5-ol was prepared as follows.

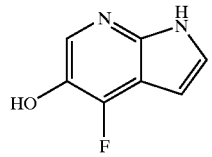

E. 1H-Pyrrolo[2,3-b]pyridine-7-oxide (50 g, 1 eq.) and tetramethylammonium bromide (86 g, 1.5 eq.) were placed in DMF (500 mL). The mixture was cooled to 0° C. and methanesulfonic anhydride (130 g, 2 eq.) was added in small portions. The suspension was allowed to reach 23° C. and stirred for 4 h. The mixture was poured in water (1L) and the solution was neutralized with an aqueous solution of 50% sodium hydroxide (pH=7). Water (2L) was added and the mixture was cooled to 10° C. for 30 min. The solid formed was filtered and washed with cooled water (1L). The solid was dissolved in a mixture of dichloromethane/methanol (4:1), dried over MgSO$_4$, concentrated in vacuo to afford 4-bromo-1H-pyrrolo[2,3-b]pyridine (40 g, 54%). $^1$H NMR (400 MHz, DMSO-$d_6$) δ 12.05 (1H, br. s), 8.08 (1H, d, J=5.3 Hz), 7.59 (1H, m), 7.33 (1H, d, J=5.05 Hz), 6.41 (1H, d, J=3.5 Hz). LCMS; m/z 197 (M+H)$^+$.

F. A 500-mL oven-dried flask capped with a rubber septum was evacuated and backfilled with argon. The flask was charged with 4-bromo-1H-pyrrolo [2,3-b]pyridine (40 g, 1 eq.) and THF (400 mL). The mixture was cooled to 0° C. and sodium hydride (60% in oil, washed with hexanes, 8.9 g, 1 eq) was added in small portions. After 15 min, chloro-triisopropylsilane (443.4 mL, 1 eq) was added, the tube was sealed and stirred at 80° C. for 3 h. The reaction mixture was cooled down, neutralized with saturated ammonium chloride (50 mL) and extracted twice with hexanes (2×800 mL). Combined organic layers were dried, and concentrated in vacuo to afford 4-bromo-1-triisopropylsilanyl-1H-pyrrolo[2,3-b]pyridine (71.1 g, 99%). $^1$H NMR (400 MHz, DMSO-$d_6$) δ 8.09 (1H, d, J=5.1 Hz), 7.60 (1H, d, J=3.5 Hz), 7.37 (1H, d, J=5.3 Hz), 6.59 (1H, d, J=3.5 Hz), 1.85 (3H, septu. J=7.6 Hz), 1.04 (9H, d, J=7.6 Hz). LCMS; m/z 353 (M+H$^+$).

G. An 250 mL oven-dried round-bottom flask was evacuated and backfilled with Argon. The flask was charged 4-bromo-1-triisopropylsilanyl-1H-pyrrolo[2,3-b]pyridine (1.4 g, 1 eq), THF (25 mL) and the mixture was cooled to −78° C. Tert-butyllithium (1.7 M in pentane, 4.66 mL, 2 eq.) was added dropwise and after 5 minutes, N-fluorobenzenesulfonimide (1.25 g, 1 eq.) was added. After 45 min, a solution of saturated ammonium chloride (20 mL) was added and the mixture was allowed to reach RT. Water was added (40 mL) and the solution was extracted with hexanes (3×100 mL), combined organic layers were washed with water, dried over MgSO$_4$ and concentrated in vacuo. The crude material was purified by flash chromatography eluting a mixture of 100% hexanes to give 4-fluoro-1-triisopropylsilanyl-1H-pyrrolo[2,3-b]pyridine (970 mg, 84%).

H. Procedures described in Example 4E and 4F were then followed to obtain the title compound.

The following examples were prepared using a procedure similar to that described for the preparation of Example 7 by employing the appropriate hydroxyazaindole and the appropriate pyrrolotriazine which, in turn, was prepared using the three-step sequence (A→B→C) described above with the appropriate modification in step B. Compounds are shown below in Table 1.

TABLE 1

| Ex. | R₂ | R₃ | Name | LC/MS (M + H)⁺ | Yield (%) |
|---|---|---|---|---|---|
| 8 | (R)-MeCH(OH)CH₂O | Me | (R)-1-[4-(4-Fluoro-2-methyl-1H-pyrrolo[2,3-b]pyridin-5-yloxy)-5-methyl-pyrrolo[2,1-f][1,2,4]triazin-6-yloxy]-propan-2-ol | 372 | 25 |
| 9 | (S)-MeCH(OH)CH₂O | H | (S)-1-[4-(4-Fluoro-1H-pyrrolo[2,3-b]pyridin-5-yloxy)-5-methylpyrrolo[2,1-f][1,2,4]triazin-6-yloxy]-propan-2-ol | 388 | 36 |
| 10 | (S)-MeCH(OH)CH₂O | Me | (S)-1-[4-(4-Fluoro-2-methyl-1H-pyrrolo[2,3-b]pyridin-5-yloxy)-5-methylpyrrolo[2,1-f][1,2,4]triazin-6-yloxy]-propan-2-ol | 372 | 37 |
| 11 | (R)-MeCH(OBn)CH₂O | H | (R)-6-(2-Benzyloxy-propoxy)-4-(4-fluoro-1H-pyrrolo[2,3-b]pyridin-5-yloxy)-5-methylpyrrolo[2,1-f][1,2,4]triazine | 448 | 61 |
| 12 | (R)-MeOCH₂CH(OH)CH₂O | H | (R)-1-[4-(4-Fluoro-1H-pyrrolo[2,3-b]pyridin-5-yloxy)-5-methylpyrrolo[2,1-f][1,2,4]triazin-6-yloxy]-3-methoxypropan-2-ol | 388 | 64 |
| 12 | (R)-MeOCH₂CH(OH)CH₂O | Me | (R)-1-[4-(4-Fluoro-2-methyl-1H-pyrrolo[2,3-b]pyridin-5-yloxy)-5-methylpyrrolo[2,1-f][1,2,4]triazin-6-yloxy]-3-methoxy-propan-2-ol | 402 | 14 |
| 13 | (S)-MeOCH₂CH(OH)CH₂O | H | (S)-1-[4-(4-Fluoro-1H-pyrrolo[2,3-b]pyridin-5-yloxy)-5-methylpyrrolo[2,1-f][1,2,4]triazin-6-yloxy]-3-methoxypropan-2-ol | 358 | 33 |
| 14 | (S)-MeOCH₂CH(OH)CH₂O | Me | (S)-1-[4-(4-Fluoro-2-methyl-1H-pyrrolo[2,3-b]pyridin-5-yloxy)-5-methylpyrrolo[2,1-f][1,2,4]triazin-6-yloxy]-3-methoxypropan-2-ol | 402 | 28 |
| 15 | NH₂SO₂NH(CH₂)₂O | H | N-{2-[4-(4-Fluoro-1H-pyrrolo[2,3-b]pyridin-5-yloxy)-5-methylpyrrolo[2,1-f][1,2,4]triazin-6-yloxy]-ethyl}-sulfamide | 422 | 48 |

TABLE 1-continued

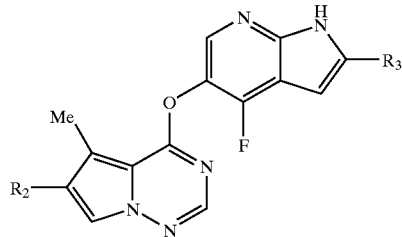

| Ex. | R₂ | R₃ | Name | LC/MS (M + H)⁺ | Yield (%) |
|---|---|---|---|---|---|
| 16 | MeSO₂NH(CH₂)₂O | H | N-{2-[4-(4-Fluoro-1H-pyrrolo[2,3-b]pyridin-5-yloxy)-5-methyl-pyrrolo[2,1-f][1,2,4]triazin-6-yloxy]-ethyl}-methanesulfonamide | 421 | 40 |
| 17 | MeSO₂NH(CH₂)₂O | Me | N-{2-[4-(4-Fluoro-2-methyl-1H-pyrrolo[2,3-b]pyridin-5-yloxy)-5-methyl-pyrrolo[2,1-f][1,2,4]triazin-6-yloxy]-ethyl}-methanesulfonamide | 435 | 15 |

The 4-fluoro-2-methyl-5-hydroxy-1H-pyrrolo[2,3-b]pyridine needed for examples 8, 10, 12, 14, and 17 was prepared from 4-fluoro-2-methyl-1-triisopropylsilanyl-1H-pyrrolo[2,3-b]pyridine as described in Example 4. The latter compound was prepared as follows.

Preparation of 4-Fluoro-2-methyl-1-triisopropylsilanyl-1H-pyrrolo[2,3-b]pyridine

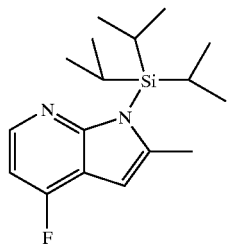

A. To a solution of 4-fluoro-1H-pyrrolo[2,3-b]pyridine (408 mg, 3.0 mmol), in THF (5 mL) sodium hydride (60% in oil, 120 mg, 3.0 mmol) was added in small portions. After 30 min, benzenesulfonyl chloride (0.42 mL, 3.3 mmol) was added and stirred at 23° C. for 21 h. Ethyl acetate was added (25 mL), the mixture was cooled at 0° C., neutralized with a solution of saturated ammonium chloride and layers were separated. The aqueous layer was extracted twice with ethyl acetate (2×25 mL), the organic layers were combined, washed with water (100 mL), brine (100 mL), dried, and concentrated in vacuo. The crude material was purified by flash chromatography eluting with 25% ethyl acetate in hexane to give of 1-benzenesulfonyl-4-fluoro-1H-pyrrolo[2,3-b]pyridine (683 mg, 82%). ¹H NMR (400 MHz, DMSO-d₆) δ 8.40 (1H, dd, J=5.8, 7.8 Hz), 8.12 (2H, dd, J=1.0, 6.3 Hz), 7.98 (1H, d, J=4.3 Hz), 7.73 (1H, tt, J=1.3, 6.9 Hz), 7.63 (3H, t, J=7.3 Hz), 7.25 (1H, dd, J=5.6, 9.9 Hz), 6.93 (1H, d, J=4.1 Hz). LCMS m/z 277 (M+H⁺).

B. To a solution of 1-benzenesulfonyl-4-fluoro-1H-pyrrolo[2,3-b]pyridine (683 mg, 2.47 mmol), in THF (12.0 mL) at −78° C., n-butyllithium solution (2.36M in hexanes, 2.30 mL, 5.44 mmol) was added dropwise. After 90 min, iodomethane (0.31 mL, 4.95 mmol) was added rapidly. After 15 min, a solution of saturated ammonium chloride was added and the mixture was allowed to reach RT. The solution was extracted with ethyl acetate (3×15 mL), combined organic layers were washed with water (30 mL), brine (30 mL), dried, and concentrated in vacuo. The crude material was placed in of THF (12 mL) and a solution tetrabutylammonium fluoride (1.0 M in THF, 3.7 mL, 3.7 mmol) was added. The mixture was heated at 65° C. for 16 h. The mixture was cooled RT, concentrated in vacuo and the residue was purified by preparative HPLC to yield 4-fluoro-2-methyl-1H-pyrrolo[2,3-b]pyridine (300 mg, 80%). ¹H NMR (400 MHz, CDCl₃) δ 10.70 (1H, s), 8.13 (1H, t, J=5.8 Hz), 6.77 (1H, dd, J=5.3, 9.6 Hz), 6.25 (1H, s) 2.51 (3H, s). LCMS; m/z 151 (M+H⁺).

C. To a solution of 4-fluoro-2-methyl-1H-pyrrolo[2,3-b]pyridine (300 mg, 2.0 mmol), in THF (6 mL), sodium hydride (60% in oil, 84 mg, 2.1 mmol) was added in small portions. After 30 min, chlorotriisopropylsilane (0.45 mL, 2.1 mmol) was added and the mixture was stirred at 65° C. for 16 h. Ethyl acetate was added (25 mL), the mixture was cooled at 0° C., neutralized with a solution of saturated ammonium chloride and layers were separated. The aqueous layer was extracted twice with ethyl acetate (2×25 mL), the organic layers were combined, washed with water (100 mL), brine (100 mL), and concentrated in vacuo. The crude material was purified by flash chromatography eluting with hexanes to give 4-fluoro-2-methyl-1-triisopropylsilanyl-1H-pyrrolo[2,3-b]pyridine (400 mg, 65%) as a colorless oil. LCMS; m/z 307 (M+H⁺).

EXAMPLE 18

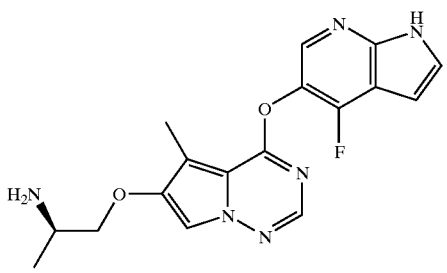

(R)-2-[4-(4-Fluoro-1H-pyrrolo[2,3-b]pyridin-5-yloxy)-5-methylpyrrolo[2,1-f][1,2,4]triazin-6-yloxy]-1-methylethylamine A. Procedures given in *Tetrahedron Lett*, 1977, 1977, and *JACS*, 1999, 3637 were modified. Thus, a 10 mL flask was charged with 1-(5-methyl-4-methylsulfanylpyrrolo[2,1-f][1,2,4]triazin-6-yloxy)-propan-2-ol (249 mg, 0.98 mmol), and tetrahydrofuran (4.91 mL) and cooled to 0° C. Triphenylphosphine (516 mg, 1.96 mmoles), diethyl azodicarboxylate (310 μL, 1.96 mmol) and diphenylphosphoryl azide (424 μL, 1.96 mmol) were added in order. The mixture was stirred at 23° C. for 15 h and then concentrated in vacuo. The crude material was purified by flash chromatography eluting with a mixture of 20% ethyl acetate in hexane to give (156 mg, 57%) of 6-(2-azidopropoxy)-5-methyl-4-methylsulfanylpyrrolo[2,1-f][1,2,4]triazine as white solid. $^1$H NMR (400 MHz, DMSO-$d_6$) δ 8.19 (1H, s), 7.85 (1H, s), 4.16 (1H, dd, J=2.8, 9.6 Hz), 4.05–3.96 (m, 2H), 2.60 (3H, s), 2.37 (3H, s), 1.21 (3H, d, J=6.3 Hz). LCMS m/z 254 (M+H$^+$).

B. 6-(2-Azido-propoxy)-5-methyl-4-methylsulfanyl-pyrrolo[2,1-f][1,2,4]triazine and 4-fluoro-1H-pyrrolo[2,3-b]pyridin-5-ol were reacted together according to the procedure described in Example 7 to afford 6-(2-azido-propoxy)-4-(4-fluoro-1H-pyrrolo[2,3-b]pyridin-5-yloxy)-5-methyl-pyrrolo[2,1-f][1,2,4]triazine. The crude material was purified by preparative HPLC. $^1$H NMR (400 MHz, DMSO-$d_6$) δ 12.18 (1H, s), 8.32 (1H, d, J=9.6 Hz), 8.02 (1H, s) 7.96 (1H, s), 6.60 (1H, d, J=3.6 Hz), 4.21 (1H, d, J=7.0 Hz), 4.09–4.02 (2H, m), 2.42 (3H, s), 1.23 (3H, d, J=6.3 Hz). LCMS m/z 382 (M+H$^+$).

C. A solution of 6-(2-azido-propoxy)-4-(4-fluoro-1H-pyrrolo[2,3-b]pyridin-5-yloxy)-5-methyl-pyrrolo[2,1-f][1,2,4]triazine (20 mg, 0.05 mmol) in ethyl acetate (2.0 mL) was stirred in the presence of hydrogen (14 psi) and 10% Pd/C (10 mg) for 12 h. Excess hydrogen was removed and the mixture was filtered through Celite® and evaporated. The residue was purified by preparative HPLC to afford (10 mg, 54%) of the title compound. LCMS: m/z 357 (M+H$^+$). Dihydrochloride salt: $^1$H NMR (400 MHz, DMSO-$d_6$) δ 12.19 (1H, s), 8.31 (1H, d, J=8.9 Hz), 8.16 (2H, br. s), 8.05 (1H, m), s), 7.97 (1H, s), 7.60 (1H, s), 6.60 (1H, s), 4.19 (2H, m), 4.03 (2H, m), 3.65 (1H, m), 1.30 (3H, d, J=6.8 Hz).

EXAMPLE 19

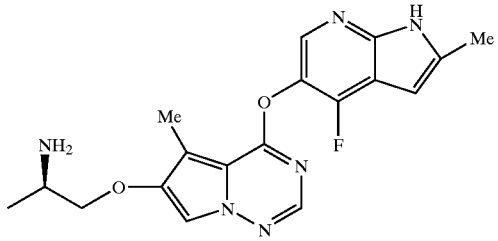

(R)-2-[4-(4-Fluoro-2-methyl-1H-pyrrolo[2,3-b]pyridin-5-yloxy)-5-methylpyrrolo[2,1-f][1,2,4]triazin-6-yloxy]-1-methyl-ethylamine Compound A of example 18 was treated with 4-fluoro-2-methyl-1H-pyrrolo[2,3-b]pyridin-5-ol followed by reduction of azide as described in the preparation of example 18 afforded the title compound. The product was purified by preparative HPLC. LCMS; m/z 371 (M+H$^+$). Dihydrochloride salt: $^1$H NMR (400 MHz, DMSO-$d_6$) δ 7.97 (1H, d, J=8.9 Hz), 7.71 (1H, s), 7.64 (1H, s), 6.20 (1H, s), 4.09 (1H, dd, J=10.1, 3.8 Hz), 3.93 (1H, dd, J=10.1, 3.8 Hz), 3.59 (1H, m), 3.21 (2H, m), 2.43 (3H, s), 1.81 (3H, s), 1.30 (3H, d, J=6.8 Hz).

EXAMPLE 20

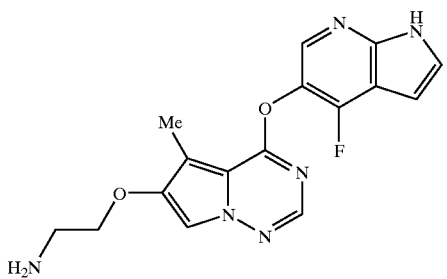

2-[4-(4-Fluoro-1H-pyrrolo[2,3-b]pyridin-5-yloxy)-5-methylpyrrolo[2,1-f][1,2,4]triazin-6-yloxy]-ethylamine A. A 25 mL flask was charged with 5-methyl-4-phenoxypyrrolo[2,1-f][1,2,4]triazin-6-ol (450 mg, 1.87 mmol, WO 0071129), (2-hydroxyethyl)-carbamic acid tert-butyl ester (577 μL, 3.73 mmol), tetrahydrofuran (9.3 mL) and cooled to 0° C. Triphenylphosphine (978 mg, 3.73 mmol), diethyl azodicarboxylate (310 µL, 1.96 mmol) were then added. The mixture was stirred at 23° C. for 15 h then concentrated in vacuo. The crude material was purified by flash chromatography eluting with a mixture of 20% ethyl acetate in hexane to give [2-(5-methyl-4-phenoxypyrrolo[2,1-f][1,2,4]triazin-6-yloxy)-ethyl]-carbamic acid tert-butyl ester. $^1$H NMR (400 MHz, DMSO-$d_6$) δ 8.98 (1H, s), 7.93 (1H, s), 7.89 (1H, s), 7.46 (2H, t, J=4.5 Hz), 7.30 (2H, d, J=8.4 Hz), 7.04 (1H, t, J=5.6 Hz), 4.05–3.98 (4H, m), 2.36 (3H, s), 1.38 (9H, s). LCMS; m/z 385 (M+H$^+$).

B. The procedure described in Step A of Example 7 was applied starting with (865 mg, 2.25 mmol) of [2-(5-methyl-4-phenoxypyrrolo[2,1-f][1,2,4]triazin-6-yloxy)-ethyl]-carbamic acid tert-butyl ester to afford [2-(5-methyl-4-methylsulfanyl-pyrrolo[2,1-f][1,2,4]triazin-6-yloxy)-ethyl]-carbamic acid tert-butyl ester (652.7 mg, 86%). $^1$H NMR (400 MHz, DMSO-$d_6$) δ 8.98 (1H, s), 8.17 (1H, s), 7.79 (1H, s), 7.02 (1H, t, J=5.6 Hz), 4.02 (2H, q, J=7.3 Hz), 3.96 (2H, t, J=5.6 Hz), 2.59 (3H, s), 2.35 (3H, s), 1.37 (9H, s). LCMS; m/z 339 (M+H$^+$).

C. The procedure described in Example 7 was employed starting with (100 mg, 0.30 mmol) of [2-(5-methyl-4-methylsulfanylpyrrolo[2,1-f][1,2,4]triazin-6-yloxy)-ethyl]-carbamic acid tert-butyl ester to afford {2-[4-(4-Fluoro-1H-pyrrolo[2,3-b]pyridin-5-yloxy)-5-methyl-pyrrolo[2,1-f][1,2,4]triazin-6-yloxy]-ethyl}-carbamic acid tert-butyl ester (42 mg, 73%). $^1$H NMR (400 MHz, DMSO-$d_6$) δ 12.17 (1H, s), 8.31 (1H, d, J=9.3 Hz), 7.96 (1H, s), 7.94 (1H, s), 7.62 (1H, s), 7.05 (1H, m), 6.60 (1H, s), 4.02 (2H, m), 3.32 (2H, m), 2.40 (3H, s), 1.38 (9H, s). LCMS; m/z 443 (M+H$^+$).

D. To a solution of {2-[4-(4-fluoro-1H-pyrrolo[2,3-b]pyridin-5-yloxy)-5-methylpyrrolo[2,1-f][1,2,4]triazin-6-yloxy]-ethyl}-carbamic acid tert-butyl ester (30 mg, 0.068 mmol) in dichloromethane (1.4 mL) was added the trifluoroacetic acid (0.14 mL) at RT. After 160 min, the mixture was concentrated and the residue was purified by preparative HPLC and, after concentration, the hydrochloride salt was made using a 1N aqueous solution of HCl in acetonitrile and the salt was lyophilized to afford of 2-[4-(4-fluoro-1H-pyrrolo[2,3-b]pyridin-5-yloxy)-5-methylpyrrolo[2,1-f][1,2,4]triazin-6-yloxy]-ethylamine (14.1 mg, 53%) as a white lyophilate. $^1$H NMR (400 MHz, DMSO-$d_6$) δ 12.19 (1H, s), 8.31 (1H, d, J=9.6 Hz), 8.13 (3H, broad s), 8.05 (1H, s), 7.97 (1H, s), 7.62 (1H, t, J=3.0 Hz), 6.59 (1H, dd, J=1.8, 3.5 Hz), 4.24 (2H, t, J=4.8 Hz), 3.26 (2H, q, J=5.3 Hz), 2.47 (3H, s). LCMS; m/z 343 (M+H$^+$). HRMS calculated for $C_{16}H_{15}FN_6O_2$: 343.1318, found: 343.1309.

The following examples were prepared using a procedure similar to that described for the preparation of Example 7 using the appropriate hydroxyazaindole. However, the sulfone of Example 7 is replaced in the following examples by the appropriate chloroimidate. See Example 25 for the preparation of 5-isopropylpyrrolo[2,1-f]-triazine that is required for Example 22.

TABLE 2

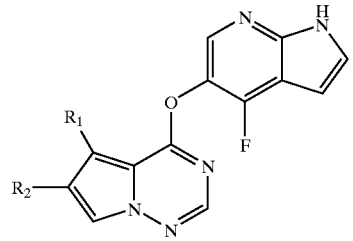

| Ex. | $R_1$ | $R_2$ | Name | LC/MS (M + H)$^+$ | Yield (%) |
|---|---|---|---|---|---|
| 21 | Me | COOEt | 4-(4-Fluoro-1H-pyrrolo[2,3-b]pyridin-5-yloxy)-5-methylpyrrolo[2,1-f][1,2,4]triazine-6-carboxylic acid ethyl ester | 356 | 24 |
| 22 | i-Pr | COOMe | 4-(4-Fluoro-1H-pyrrolo[2,3-b]pyridin-5-yloxy)-5-isopropylpyrrolo[2,1-f][1,2,4]triazine-6-carboxylic acid methyl ester | 370 | 33 |

EXAMPLE 23

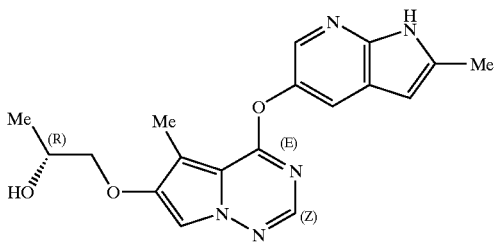

(R)-1-[5-Methyl-4-)2-methyl-1H-pyrrolo[2,3-b]pyridin-5-yloxy)-pyrrolo[2,1-f][1,2,4]triazin-6yloxy]-propan-2-ol The sulfone, 1-(4-methanesulfonyl-5-methyl-pyrrolo[2,1-f][1,2,4]triazin-6-yloxy)-propan-2-ol, was coupled with 4-fluoro-2-methyl-1H-pyrrolo[2,3-b]pyridin-5-ol according to the procedure described in Example 4 (55% yield). LCMS; m/z 354 (M+H$^+$), Dihydrochloride salt: $^1$H NMR (400 MHz, DMSO-d$_6$) δ 11.65 (1H, s), 8.04 (1H, s), 7.90 (1H, s), 7.87 (1H, s), 7.75 (1H, s), 6.17 (1H, s), 4.33 (1H, m), 3.98 (1H, m), 3.85 (2H, m), 2.49 (3H, s), 2.40 (3H, s), 1.16 (3H, d, J=6.8 Hz).

EXAMPLE 24

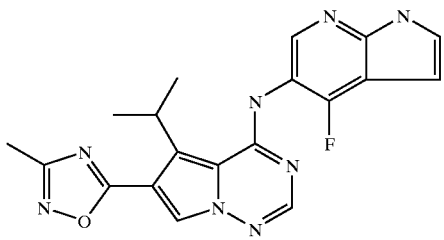

(4-Fluoro-1H-pyrrolo[2,3-b]pyridin-5-yl)-[5-isopropyl-6-(3-methyl-[1,2,4]oxadiazol-5-yl)-pyrrolo[2,1-f][1,2,4]triazin-4-yl]-amine A. To a solution of N-hydroxyacetamidine (315 mg, 4.25 mmol) in of THF (10 mL) at 0° C. was added sodium hydride (60% in oil, 340 mg, 8.5 mmol) in small portions and the resulting mixture was stirred for 20 min. 5-Isopropyl-4-oxo-3,4-dihydro-pyrrolo[2,1-f][1,2,4]triazine-6-carboxylic acid methyl ester was then added and the mixture was heated in a pressure vessel at 80° C. for 18 h. The reaction mixture was cooled down and the precipitate was filtered and. The filtrate was diluted with ethyl acetate and washed with saturated ammonium chloride, brine (50 mL), dried (MgSO$_4$), filtered and concentrated to afford 5-isopropyl-6-(3-methyl-[1,2,4]oxadiazol-5-yl)-3H-pyrrolo[2,1-f][1,2,4]triazin-4-one (520 mg, 95%).

B. To a solution of oxadiazole from previous step (300 mg, 1.08 mmol) in toluene (7 mL) were added phosphorus oxychloride (122 μL, 1.29 mmol) and diisopropylethylamine (150 μL, 0.86 mmol) and the reaction mixture was heated to reflux for 3 days. The reaction mixture was cooled down and poured over ice-cooled saturated sodium bicarbonate solution. The separated aqueous layer was extracted with ethyl acetate (2×25 mL) and the combined organic layers were washed with brine (50 mL), dried (MgSO$_4$.), filtered and evaporated to afford crude 4-chloro-5-isopropyl-6-(3-methyl-[1,2,4]oxadiazol-5-yl)-pyrrolo[2,1-f][1,2,4]triazine which was directly used in next step (280 mg, 94%).

C. Diisopropylethylamine (0.1 mL, 0.5 mmol) was added to a solution of 4-chloro-5-isopropyl-6-(3-methyl-[1,2,4]oxadiazol-5-yl)-pyrrolo[2,1-f][1,2,4]triazine (54 mg, 0.18 mmol, see Example 25) and 4-fluoro-1H-pyrrolo[2,3-b]pyridin-5-ylamine (30 mg, 0.18 mmol) in DMF (1.0 mL). The mixture was stirred at RT for 16 h., quenched with saturated ammonium chloride (20 mL) and extracted with ethyl acetate (3×25 mL). The combined organic layers were washed with brine (50 mL), dried, filtered and concentrated. The residue was purified by preparative HPLC to afford the title compound (34 mg, 43%). LCMS : m/z 393 (M+H)$^+$. Monohydrochloride salt: $^1$H NMR (400 MHz, DMSO-d$_6$) δ 11.99 (1H, s), 8.12 (1H, s.), 7.89 (1H, s), 7.50 (1H, s), 6.55 (1H, br. s.), 4.16 (1H, m), 2.43 (3H, s), 144 (6H, d, J=7.3 Hz).

The intermediate, 4-Fluoro-1H-pyrrolo[2,3-b]pyridin-5-ylamine was prepared as follows:

D. A 100 mL oven-dried round-bottom flask was evacuated and backfilled with Argon. The flask was charged with 4-fluoro-1-triisopropylsilanyl-1H-pyrrolo[2,3-b]pyridine (763 mg, 2.61 mmol), THF (17.4 mL) and the mixture was cooled to −78° C. A solution of sec-butyllithium (1.10 M in THF, 5.21 mL, 5.74 mmol) was added dropwise and after 30 minutes, 1-sulfonylazido-4-methylbenzene (1.29 g, 6.52 mmol) in THF (7.4 mL) was added rapidly. After 25 min, a solution of saturated ammonium chloride was added and the mixture was allowed to reach RT. The mixture was extracted with ethyl acetate (3×50 mL), combined organic layers were washed with water (100 mL), brine (100 mL), dried and concentrated in vacuo. The crude material was stirred in hexanes to remove the excess of 1-azido-4-methylbenzene and the filtrate was purified by flash chromatography eluting a mixture of 2.5% ethyl acetate in hexanes to give 5-azido-4-fluoro-1-triisopropylsilanyl-1H-pyrrolo[2,3-b]pyridine (746 mg, 86%) as a colorless oil. $^1$H NMR (400 MHz, DMSO-d$_6$) δ 8.16 (1H, d, J=10.3 Hz), 7.56 (1H, d, J=3.3 Hz), 6.71 (1H, d, J=3.6 Hz) 1.84 (3H, m), 1.05 (9H, s), 1.03 (9H, s). LCMS: m/z 334 (M+H$^+$), E. The procedure described for desilylation in Example 7 was applied to afford 5-azido-4-fluoro-1H-pyrrolo[2,3-b]pyridine. $^1$H NMR (400 MHz, DMSO-d$_6$) δ 12.10 (1H, s), 8.14 (1H, d, J=10.1 Hz), 7.57 (1H, t, J=2.5 Hz), 6.53 (1H, dd, J=1.8, 3.3 Hz). LCMS; m/z 178 (M+H).

F. The procedure for conversion of azide group to amine group described in example 18 was applied to 5-azido-4-fluoro-1H-pyrrolo[2,3-b]pyridine using 45 p.s.i. of hydrogen to afford 4-fluoro-1H-pyrrolo[2,3-b]pyridin-5-ylamine (91% yield) as a tan solid. $^1$H NMR (400 MHz, DMSO-d$_6$) δ 11.42 (1H, s), 7.84 (1H, d, J=10.9 Hz), 7.30 (1H, t, J=3.0 Hz), 6.28 (1H, dd, J=1.9, 3.6 Hz). LCMS; m/z 152 (M+H$^+$). HRMS calculated for C$_7$H$_6$FN$_3$: 151.0545, found: 151.0549

EXAMPLE 25

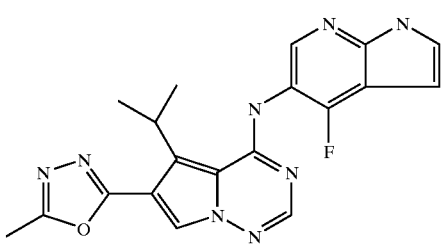

(4-Fluoro-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine A. Ethyl isocyanoacetate (80 g, 0.71 moles) was dissolved in 1 L of dry tetrahydrofuran under nitrogen and 1,8- diazabicyclo[5.4.0]undec-7-ene (107.7 g, 0.71 moles) was added to the solution. A solution of isobutyraldehyde (29.7 g, 0.41 moles) in 1.5 L of dry tetrahydrofuran was added dropwise at room temperature over 3 hours. The mixture was then stirred at room temperature for 16 h. The reaction mixture was concentrated under vacuum to a brown oil. The concentrate was partitioned between 1.2 L of ethyl acetate and 0.5 L of water. The organic layer was then washed with 0.4 L of 0.1 N hydrochloric acid followed by 0.3 L of saturated sodium bicarbonate solution and then 0.3 L of saturated brine. The organic layer was dried (sodium sulfate), filtered and concentrated under vacuum to a brown oil. The residue was dissolved in toluene and added to a 1600 ml (~800 g) column of silica gel wet with hexane. Product was eluted at 15 PSI nitrogen pressure first with 4.8 L of hexane followed by 5 L of 20% ethyl acetate in hexane. Eluent containing product by TLC analysis was combined and concentrated under vacuum to a yellow oil. The concentrate was pumped dry under high vacuum giving product A, 3-(1-methylethyl)pyrrole-2,4-dicarboxylic acid diethyl ester (54 g, 60% yield) of yellow oil that solidified on standing at room temperature. TLC silica gel: $R_f$=0.2, hexane/ethyl acetate (4/1) uv visualization and PMA stain. $^1$H NMR: (CDCl$_3$) δ 1.2–1.5 (m, 12H), 4.2–4.3 (m, 1H), 4.3–4.3 (m, 4H), 7.5 (d, 1H).

B. To a suspension of NaH (13.9 g, 34 mmol, 60% in oil) in DMF (0.36 L) at 0° C. was added a solution of compound A (75 g, 29 mmol) in DMF (0.4 L). After stirring for 45 min., 2,4-dinitrohydroxylamine was added in small portions. After the addition was complete, the cold bath was removed and the mixture was allowed to warm to room temperature. After 2 h., the reaction mixture was poured into water and extracted with ethyl acetate. The organic layer was washed with saturated sodium bicarbonate, 10% lithium chloride (LiCl) and brine, then dried, and concentrated. The residue was purified to afford the desired compound 1-amino-3-(1-methylethyl)pyrrole-2,4-dicarboxylic acid diethyl ester, as an oil (81 g) at 80% purity which was used without further purification.

C. Compound B (77.7 g, 0.29 M) was mixed with formamide (0.5 L) and heated to 160° C. After 8 h., the mixture was allowed to cool to RT, stirred for 2 days and then diluted with water (4 L). The product was extracted with ethyl acetate. The organic layer was concentrated, toluene was added to the residue and concentrated again. The brown solid was triturated with ether and dried under high vacuum to afford 5-(1-methylethyl)pyrrolo[2,1-f][1,2,4]triazin-4 (3H)-one-6-carboxylic acid ethyl ester, as a light brown solid (45 g, 62%). LC/MS; (M+H)$^+$=250.1

D. A suspension of 5-isopropyl-4-oxo-3,4-dihydro-pyrrolo [2,1-f][1,2,4]triazine-6-carboxylic acid ethyl ester was suspended in water (4 mL) and hydrazine hydrate (4 mL) was heated at 110° C. for 24 h. The reaction mixture was cooled down and the precipitate formed was isolated by filtration and air dried. The solid was suspended in ethyl acetate and acetyl chloride (853 μL, 12 mmol) was added. The mixture was stirred at RT for 2 days and the solid was isolated by filtration, washed with ethyl acetate and air-dried to afford 5-isopropyl-6-(5-methyl-[1,3,4]oxadiazol-2-yl)-3H-pyrrolo [2,1-f][1,2,4]triazin-4-one (575 mg, 35%).

E. The procedure for chloroimidate formation described in Example 24 was used to convert 5-isopropyl-6-(5-methyl-[1,3,4]oxadiazol-2-yl)-3H-pyrrolo[2,1-f][1,2,4]triazin-4-one to 4-chloro-5-isopropyl-6-(5-methyl-[1,3,4]oxadiazol-2-yl)-pyrrolo[2,1-f][1,2,4]triazine in quantitative yield which was used directly without any purification.

F. The procedure described in example 24 for coupling of aniline was employed to react 4-chloro-5-isopropyl-6-(5-methyl-[1,3,4]oxadiazol-2-yl)-pyrrolo[2,1-f][1,2,4]triazine and 4-fluoro-1H-pyrrolo[2,3-b]pyridin-5-ylamine to afford the title compound (41% yield). Monohydrochloride salt: $^1$H NMR (400 MHz, MeOD-d$_4$) δ 8.26 (1H, s.), 8.00 (1H, s), 7.50 (1H, m), 6.69 (1H, m.), 4.08 (1H, m), 2.51 (3H, s), 1.40 (6H, d, J=7.1 Hz).

The following examples were prepared by employing the coupling procedure exemplified in Example 24. Examples 26 and 27 were prepared using a procedure similar to that described for the preparation of Example 24 and 25, respectively, by using the appropriate 5-aminoazaindole. Example 28 was made in a similar way to that of Example 18.

TABLE 3

| Ex | R$_1$ | R$_2$ | R$_3$ | Name | LC/MS (M + H)$^+$ | Yield (%) |
|---|---|---|---|---|---|---|
| 26 | i-Pr | 5-methyl-[1,3,4]oxadiazol-2-yl | Me | (4-Fluoro-2-methyl-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine | 407 | 26 |

TABLE 3-continued

| Ex | R₁ | R₂ | R₃ | Name | LC/MS (M + H)⁺ | Yield (%) |
|---|---|---|---|---|---|---|
| 27 | i-Pr | (3-methyl-1,2,4-oxadiazol-5-yl) | Me | (4-Fluoro-2-methyl-1H-pyrrolo[2,3-b]pyridin-5-yl)-[5-isopropyl-6-(3-methyl-[1,2,4]oxadiazol-5-yl)-pyrrolo[2,1-f][1,2,4]triazin-4-yl]-amine | 407 | 9 |
| 28 | Me | (R)-MeCH(NH₂)CH₂O | H | (R)-[6-(2-Amino-propoxy)-5-methyl-pyrrolo[2,1-f][1,2,4]triazin-4-yl]-(4-fluoro-1H-pyrrolo[2,3-b]pyridin-5-yl)-amine | 356 | 86 |
| 29 | Me | NH₂SO₂NH(CH₂)₂O | H | N-{2-[4-(4-Fluoro-1H-pyrrolo[2,3-b]pyridin-5-ylamino)-5-methyl-pyrrolo[2,1-f][1,2,4]triazin-6-yloxy]-ethyl}-sulfamide | 421 | 56 |
| 30 | Me | (R)-MeCH(OH)CH₂O | H | (R)-1-[4-(4-Fluoro-1H-pyrrolo[2,3-b]pyridin-5-ylamino)-5-methyl-pyrrolo [2,1-f][1,2,4]triazin-6-yloxy]-propan-2-ol | 357 | 20 |
| 31 | i-Pr | COOMe | H | 4-(4-Fluoro-1H-pyrrolo[2,3-b]pyridin-5-ylamino)-5-isopropylpyrrolo[2,1-f][1,2,4]triazine-6-carboxylic acid methyl ester | 369 | 40 |

EXAMPLE 32

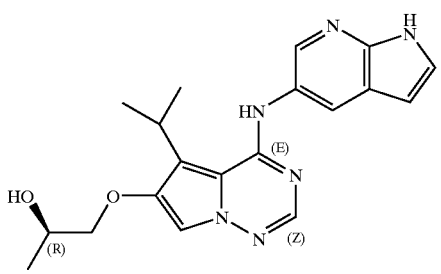

1-[5-Isopropyl-4-(1H-pyrrolo[2,3-b]pyridin-5-ylamino)-pyrrolo[2,1-f][1,2,4]triazin-6-yloxy]-propan-2-ol 1-(5-Isopropyl-4-methylsulfanylpyrrolo[2,1-f][1,2,4]triazin-6-yloxy)-propan-2-ol (262 mg, 0.93 mmol, obtained from Example 25 using procedure in Step B of Example 7) and 1-triisopropylsilanyl-1H-pyrrolo[2,3-b]pyridin-5-ylamine (290 mg, 0.93 mmol) were dissolved in chloroform and m-chloroperbenzoic acid (60%, 535 mg, 1.86 mmol) was added. The mixture was heated at 120° C. for 10 min in a Personal Chemistry Smith Enrys Optimizer™ microwave oven. The solution was evaporated in vacuo and the residue was purified by preparative HPLC. The isolated product was dissolved in of THF (10 mL) and TBAF (1.0 M, 0.2 mL, 0.2 mmol) was added. The mixture was stirred for 5 min. and the solvent was evaporated in vacuo. The residue was purified by preparative HPLC to afford the title compound (3 mg, 1%).

The intermediate, 1-triisopropylsilanyl-1H-pyrrolo[2,3-b]pyridin-5-ylamine was prepared as follows:

A. 4-Chloro-1-triisopropylsilanyl-1H-pyrrolo[2,3-b]pyridine (10 g, 32.5 mmol) was dissolved in THF (250 mL) and cooled to −78° C. Sec-Butyllithium ( 54.8 mL, 1.3M/cyclohexane, 71.4 mmol.) was then added dropwise and the solution was stirred for 20 min. A solution of tosylazide (16 g, 81.2 mmol.) in THF (100 mL) was added and the mixture was stirred for 1 h. The reaction mixture was quenched with saturated ammonium chloride (50 mL) and warmed to RT. This mixture was extracted with hexanes (2×200 mL) and the combined organic layers were dried. The organic phase was filtered and concentrated in vacuo. The crude product was purified by flash chromatography (silica gel, 100% hexanes) to afford 5-azido-4-chloro-1-triisopropylsilanyl-1H-pyrrolo[2,3-b]pyridine as a mixture with starting material (10.2 g). This mixture was directly used in next step.

B. 5-Azido-4-chloro-1-triisopropylsilanyl-1H-pyrrolo[2,3-b]pyridine (1.6 g, 4.6 mmol) was dissolved in ethyl acetate (100 mL) and Pd/C (10%, 100 mg) was added. This suspension was stirred at RT and under 1 atmosphere. of hydrogen for 18 h. The solid was removed by filtration over Celite® and the solution was evaporated in vacuo. The crude product was purified by flash chromatography (silica gel, 95% hexanes, 5% ethyl acetate) to afford 4-chloro-1-triisopropylsilanyl-1H-pyrrolo[2,3-b]pyridin-5-ylamine (730 mg, 43.5%, 2 steps).

C. 4-Chloro-1-triisopropylsilanyl-1H-pyrrolo[2,3-b]pyridin-5-ylamine (10.2 g, 31.5 mmol) was diluted in ethyl acetate (200 mL) and acetic acid (100 mL). Zinc dust (50 g, 0.8 mol.) was added in small portions at RT. After stirring the suspension at RT for 4 h, the mixture was filtered over Celite and the filtrate was slowly neutralized with saturated sodium bicarbonate and extracted with ethyl acetate (2×300 mL). The combined organic layers were dried, filtered and evaporated in vacuo. The crude product was purified by flash chromatography (silica gel, 5% ethyl acetate in hexanes) to afford 1-triisopropylsilanyl-1H-pyrrolo[2,3-b]pyridin-5-ylamine (6.38 g).

Examples 33–35 were prepared as follows: Example 33 was synthesized in a manner similar to the preparation of Example 32. Examples 34 and 35 were prepared in manner similar to the preparation of Example 24.

5-Isopropyl-4-[methyl-(1H-pyrrolo[2,3-b]pyridin-5-yl)-amino]-pyrrolo[2,1-f][1,2,4]triazine-6-carboxylic acid methyl ester The title compound was prepared in a manner similar to the preparation of Example 24 by using methyl-(1H-pyrrolo[2,3-b]pyridin-5-yl)-amine and 4-chloro-5-isopropylpyrrolo[2,1-f][1,2,4]triazine-6-carboxylic acid methyl ester. (25% yield). LCMS; m/z 365 (M+H$^+$). Monohydrochloride salt: $^1$H NMR (400 MHz, DMSO-d$_6$) δ ppm 11.73 (1H, s), 8.22 (1H, s.), 8.00 (1H, s), 7.75 (1H, s), 7.50 (1H, s), 6.40 (1H, s.), 3.70 (3H, s), 3.26 (1H, m), 2.51 (3H, s), 0.54 (6H, d, J=7.3 Hz).

The intermediate, Methyl-(1H-pyrrolo[2,3-b]pyridin-5-yl)-amine, was prepared as follows:

A. 1-Triisopropylsilanyl-1H-pyrrolo[2,3-b]pyridin-5-ylamine (375 mg, 1.3 mmol) and triethylamine (271 μL, 1.95 mmol) in dichloromethane (10 mL) was treated with di-tert-butyl dicarbonate (340 mg, 1.5 mmol) and the mixture was stirred at RT for 2.5 h., quenched with saturated ammonium chloride (20 mL) and extracted with ethyl acetate (3×25 mL). The combined organic layers were washed with brine (50 mL), dried (MgSO$_4$.), filtered and concentrated. The residue was purified by preparative HPLC.

TABLE 4

| Ex. | R$_1$ | R$_2$ | Name | LC/MS (M + H)$^+$ | Yield (%) |
|---|---|---|---|---|---|
| 33 | (R)-MeOCH$_2$CH(OH)CH$_2$O | H | (R)-1-[5-Isopropyl-4-(1H-pyrrolo[2,3-b]pyridin-5-ylamino)-pyrrolo[2,1-f][1,2,4]triazin-6-yloxy]-3-methoxy-propan-2-ol | 375 | 33 |
| 34 | COOMe | H | 5-Isopropyl-4-(1H-pyrrolo[2,3-b]pyridin-5-ylamino)-pyrrolo[2,1-f][1,2,4]triazine-6-carboxylic acid methyl ester | 351 | 36 |
| 35 | (5-methyl-1,3,4-oxadiazol-2-yl) | Me | [5-Isopropyl-6-(5-methyl-[1,3,4]oxadiazol-2-yl)-pyrrolo[2,1-f][1,2,4]triazin-4-yl]-(2-methyl-1H-pyrrolo[2,3-b]pyridin-5-yl)-amine | 389 | 86 |

EXAMPLE 36

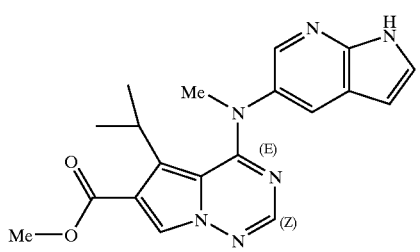

B. 1-Triisopropylsilanyl-1H-pyrrolo[2,3-b]pyridin-5-yl)-carbamic acid tert-butyl ester (250 mg, 0.6 mmol) was then treated with sodium hydride (24 mg, 60% oil, 0.6 mmol) and methyl iodide (48 mL, 0.77 mmol) in DMF (2.0 mL). The mixture was stirred at RT for 16 h, quenched with saturated ammonium chloride (20 mL) and extracted with ethyl acetate (3×25 mL). The combined organic layers were washed with brine (50 mL), dried (MgSO$_4$.), filtered and concentrated. The residue, which was used with no further purification, was then treated with TFA (1.0 mL) in dichloromethane (4.0 mL) and the mixture was stirred at RT for 10 h, concentrated and purified by preparative HPLC to afford methyl(1H-pyrrolo[2,3-b]pyridin-5-yl)-amine (31 mg, 33%). m/z 148 (M+H)$^+$.

EXAMPLE 37

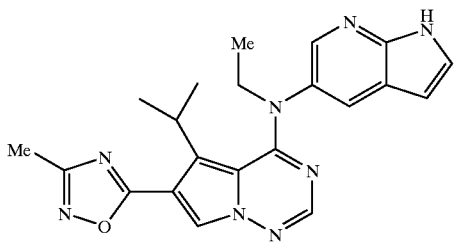

Ethyl-[5-isopropyl-6-(3-methyl-[1,2,4]oxadiazol-5-yl)-pyrrolo[2,1-f][1,2,4]triazin-4-yl]-(1H-pyrrolo[2,3-b]pyridin-5-yl)-amine The procedure described above in Example 24 was employed. Thus, when 4-chloro-5-isopropyl-6-(3-methyl-[1,2,4]oxadiazol-5-yl)-pyrrolo[2,1-f][1,2,4]triazine (86 mg, 0.31 mmol), ethyl-(1H-pyrrolo[2,3-b]pyridin-5-yl)-amine (50 mg, 0.31 mmol) and diisopropylethylamine (162 μL, 0.93 mmol) in DMF (2.0 mL) were used, the title compound was obtained. LCMS; m/z 403 (M+H)$^+$. Monohydrochloride salt: $^1$H NMR (400 MHz, DMSO-d$_6$) δ 9.70 (1H, s), 8.20 (1H, s.), 8.02 (1H, s), 7.52 (1H, s), 7.29 (1H, s), 6.38 (1H, br. s.), 4.10 (2H, q, J=6.8 Hz), 3.24(1H, m), 2.30 (3H, s), 1.19 (3H, t, J=6.8 Hz), 0.59 (6H, d, J=7.1 Hz). (1H, m), 2.30 (3H, s), 1.19 (3H, t, J=6.8 Hz), 0.59 (6H, d, J=7.1 Hz).

The intermediate, Ethyl-(1H-pyrrolo[2,3-b]pyridin-5-yl)-amine, was prepared as follows:

A. Acetyl chloride (75 μL, 1.0 mmol) was added to a solution of 1-triisopropylsilanyl-1H-pyrrolo[2,3-b]pyridin-5-ylamine (230 mg, 0.8 mmol) and 4-dimethylaminopyridine (5 mg) in pyridine (1.6 mL). The mixture was stirred at RT for 24 h and a saturated solution of ammonium chloride (30 mL) and ethyl acetate (30 mL) were added. The separated aqueous layer was extracted with ethyl acetate (3×25 mL) and the combined organic layers were dried, filtered and concentrated to provide an oil which was purified by preparative HPLC to afford N-(1-triisopropylsilanyl-1H-pyrrolo[2,3-b]pyridin-5-yl)-acetamide (140 mg, 53%) as an oil: LCMS; m/z 332 (M+H$^+$).

B. At RT under argon, a solution of borane-dimethylsulfide complex (665 μL, 6.6 mmol, 10 M) was added to N-methyl-N-(1-triisopropylsilanyl-1H-pyrrolo[2,3-b]pyridin-5-yl)-acetamide (110 mg, 0.33 mmol) in THF (3.0 mL). The mixture was heated to 65° C. for 2 h., cooled down and a 6N hydrochloric acid solution was slowly added. The mixture was heated to 100° C. and vigorously stirred for 12 h., cooled down and a 6 N sodium hydroxide solution was added until pH 7 was reached. The mixture was extracted with ethyl acetate (3×15 mL) and the combined organic layers were dried, filtered and evaporated to provide an oil which was purified through silica gel-SCX column (arylsulfonic acid with washes with methanol and 2N NH$_3$ in methanol) to afford ethyl-(1H-pyrrolo[2,3-b]pyridin-5-yl)-amine. LCMS; m/z 203 (M+AcCN), 162 (M+H)$^+$.

What is claimed is:

1. A compound selected from the group consisting of 4-(4-Fluoro-1H-pyrrolo[2,3-b]pyridin-5-yloxy)-5-methyl-pyrrolo[2,1-f][1,2,4]triazin-6-ol, (R)-1-[4-(4-Fluoro-1H-pyrrolo[2,3-b]pyridin-5-yloxy)-5-methylpyrrolo[2,1-f][1,2,4]triazin-6-yloxy]-propan-2-ol, (S)-1-[4-(4-Fluoro-1H-pyrrolo[2,3-b]pyridin-5-yloxy)-5-methyl-pyrrolo[2,1-f][1,2,4]triazin-6-yloxy]-propan-2-ol, (R)-1-[4-(4-Fluoro-2-methyl-1H-pyrrolo[2,3-b]pyridin-5-yloxy)-5-methyl-pyrrolo[2,1-f][1,2,4]triazin-6-yloxy]-propan-2-ol, (R)-2-[4-(4-Fluoro-1H-pyrrolo[2,3-b]pyridin-5-yloxy)-5-methylpyrrolo[2,1-f][1,2,4]triazin-6-yloxy]-1-methylethylamine, (R)-2-[4-(4-Fluoro-2-methyl-1H-pyrrolo[2,3-b]pyridin-5-yloxy)-5-methylpyrrolo[2,1-f][1,2,4]triazin-6-yloxy]-1-methyl-ethylamine, 2-[4-(4-Fluoro-1H-pyrrolo[2,3-b]pyridin-5-yloxy)-5-methylpyrrolo[2,1-f][1,2,4]triazin-6-yloxy]-ethylamine, (4-Fluoro-1H-pyrrolo[2,3-b]pyridin-5-yl)-[5-isopropyl-6-(3-methyl-[1,2,4]oxadiazol-5-yl)-pyrrolo[2,1-f][1,2,4]triazin-4-yl]-amine, (4-Fluoro-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine, (4-Fluoro-2-methyl-1H-pyrrolo[2,3-b]pyridin-5-yl)-[5-isopropyl-6-(5-methyl-[1,3,4]oxadiazol-2-yl)-pyrrolo[2,1-f][1,2,4]triazin-4-yl]-amine, and

[5-Isopropyl-6-(5-methyl-[1,3,4]oxadiazol-2-yl)-pyrrolo[2,1-f][1,2,4]triazin-4-yl]-(2-methyl-1H-pyrrolo[2,3-b]pyridin-5-yl)-amine.

2. A pharmaceutical composition comprising one or more of the compounds of claim 1 and a pharmaceutically acceptable carrier therefor.

* * * * *